(12) United States Patent
Figeys et al.

(10) Patent No.: US 6,864,089 B2
(45) Date of Patent: Mar. 8, 2005

(54) LABELING OF PROTEOMIC SAMPLES DURING PROTEOLYSIS FOR QUANTITATION AND SAMPLE MULTIPLEXING

(75) Inventors: Daniel Figeys, Pickering (CA); Matthias Mann, Odense (DK); Ian I. Stewart, Toronto (CA)

(73) Assignee: MDS Proteomics, Inc., Toronto (CA)

( * ) Notice: Subject to any disclaimer, the term of this patent is extended or adjusted under 35 U.S.C. 154(b) by 338 days.

(21) Appl. No.: 09/878,750

(22) Filed: Jun. 11, 2001

(65) Prior Publication Data

US 2002/0076817 A1 Jun. 20, 2002

Related U.S. Application Data

(60) Provisional application No. 60/293,664, filed on May 25, 2001, and provisional application No. 60/210,496, filed on Jun. 9, 2000.

(51) Int. Cl.$^7$ .............................................. G01N 31/00
(52) U.S. Cl. ........................ 436/6; 435/70.1; 436/173
(58) Field of Search .......................... 436/6, 173, 501, 436/57, 86, 123, 87, 89; 435/70.1, 7.1, 23, 24, 4, 69.1, 7, 183, 6; 530/350; 514/12, 18

(56) References Cited

FOREIGN PATENT DOCUMENTS

| WO | WO 99/45150   | 9/1999 |
|----|---------------|--------|
| WO | WO00/11208    | 3/2000 |
| WO | WO 00/20870   | 4/2000 |
| WO | WO 00/43792   | 7/2000 |
| WO | WO 02/056025 A2 | 7/2002 |

OTHER PUBLICATIONS

Takao et al., "Automatic Precursor–Ion Switching in a Four–Sector Tandem Mass Spectrometer and It's Application to Acquistion of the MS/MS Product Ions Derived from a Partially 18 O–Labeled Peptide for Their Facile Assignments," Anal. Chem. vol. 65, 2394–2399, 1993.

Takao et all, "Facile Assignment of Sequence Ions of a Peptide Labelled with 18O at the Carboxyl Terminus," Rapid Communications in Mass Spectrometry, vol. 5, 312–315, 1991.

Marina, A. et al. High–sensitivity Analysis and Sequencing of Peptides and Proteins by Quadrupole Ion Trap Mass Spectrometry, *J. Mass Spectrom.* 34, 17–27 (1999).

Mirgorodskaya, O. A. et al. Quantitation of peptides and proteins by matrix–assisted laser desorption/ionization mass spectrometry using $^{18}$O–labeled internal standards. *Rapid Communication Mass Spectrom.* 14, 1226–1232 (2000).

Munchbach, M. et al. Quantitation and Facilitated de Novo Sequencing of Proteins by Isotopic N–Terminal Labeling of Peptides with a Fragmentation–Directing Moiety, *Anal. Chem.* 72, 4047–4057 (2000).

Murphy, R. C. & Clay, K. L. Synthesis and Back Exchange of $^{18}$O Labeled Amino Acids for use as Internal Standards with Mass Spectrometry. *Biomed. Mass Spectrom.* 6, 309–314 (1979).

(List continued on next page.)

*Primary Examiner*—Robert A. Wax
*Assistant Examiner*—Robert B. Mondesi
(74) *Attorney, Agent, or Firm*—Ropes & Gray, LLP

(57) ABSTRACT

This invention related to methods useful in the labeling of multiple polypeptide samples and subsequent analysis of these samples by mass spectrometry, particularly in the high throughput proteomic setting.

41 Claims, 11 Drawing Sheets

OTHER PUBLICATIONS

Figure 1:
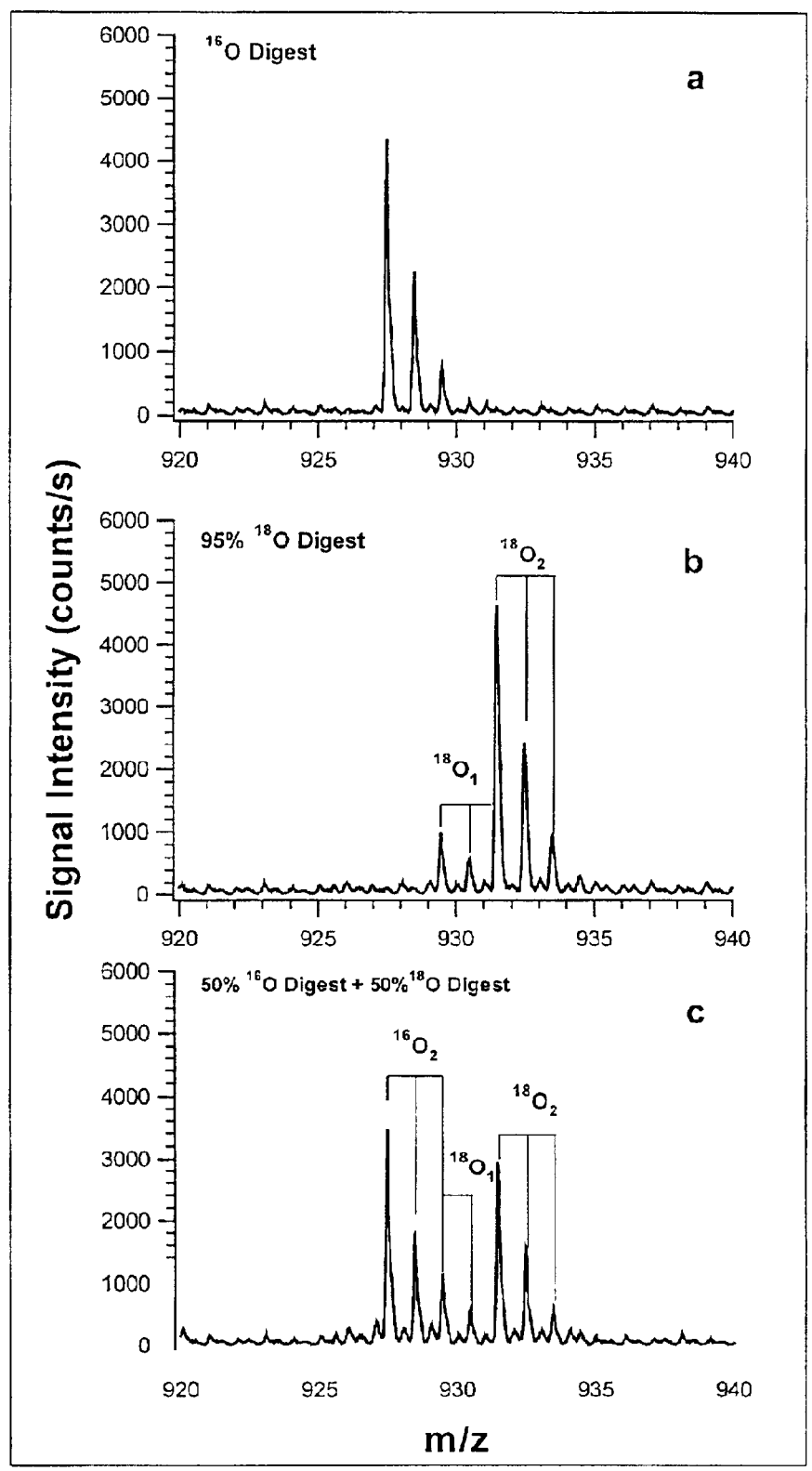

Radhakrishnan, A. & McConnell, H. M. Electric field effect on cholesterol–phospholipid complexes. *PNAS* 97, 1073–1078 (Feb. 1, 2000).

Schnolzer, M. et al. Protease–catalyzed incorporation of $^{18}$O into peptide fragments and its application for protein sequencing by electrospray and matrix–assisted laser desorption/ionization mass spectrometry. *Electrophoresis* 17, 945–953 (1996).

Sharon, N. et al. Pepsin–Catalyzed Exchange of Oxygen Atoms between Water and Carboxylic Acids. *Arch. Biochem. Biophys.* 219–221 (1962).

Shevchenko, A. et al. Charting the Proteomics of Organisms with Unsequenced Genomes by MALDI–Quadrupole Time–of–Flight Mass Spectrometry and BLAST Homology Searching. *Anal. Chem.* 73, 1917–1926 (2001).

Shevchenko, A. et al. MALDI Quadrupole Time–of–Flight Mass Spectrometry: A Powerful Tool for Proteomic Research. *Anal. Chem.* 72, 2132–2141 (May 1, 2000).

Shevchenko, A. et al. Rapid 'de Novo' Peptide Sequencing by a Combination of Nanoelectrospray, Isotopic Labeling and a Quadrupole/Time–of–flight Mass Spectrometer. *Rapid Communications in Mass Spectrom.* 11, 1015–1024 (1997).

Verhaert, P. et al. Matrix–assisted laser desorption/ionization quadrupole Time–of–Flight Mass Spectrometry: An elegant tool for peptidomics. *Proteomics 1*, 118–131 (2001).

Report on the Supply and Demand of 18O Enriched Water. Ad hoc committee of the North American Society for the Study of Obesity. (Jan. 21, 1999).

Baldwin, M. A. et al. Matrix–Assisted Laser Desorption/Ionization Coupled with Quadrupole/Orthogonal Acceleration Time–of–Flight Mass Spectrometry for Protein Discovery, Identification, and Structural Analysis. *Anal. Chem.* 73, 1707–1720 (2001).

Bender, M. L. et al. The Kinetics of the a–Chymotrypsin–catalyzed Oxygen Exchange of Carboxylic Acids. *J. Am. Chem. Soc.* 79, 116–120 (2001).

Conrads, T. P. et al. Quantitative Analysis of Bacterial and Mammalian Proteomes Using a Combination of Cysteine Affinity Tags and 15N–Metabolic Labeling. *Anal. Chem.* 73, 2132–2139 (2001).

Desiderio, D. M. & Kai, M. Preparation of Stable Isotope–Incorporated Peptide Internal Standards for Field Desorption Mass Spectrometry Quantification of Peptides in Biologic Tissue. *Biomed. Mass Spectrom.* 10, 471–479 (1983).

Griffin, T. J. et al. Quantitative Proteomic Analysis Using a Mrupole Time–of–Flight Mass Spectrometer. *Anal. Chem.* 73, 978–986 (2001).

Gygi, S. P. et al. Measuring gene expression by quantitative proteome analysis. *Curr. Opin. Biotech.* 11, 396–401 (2000).

Gygi, S. P. et al. Quantitative analysis of complex protein mixtures using isotpye–coded affinity tags. *Nature Biotech.* 17, 994–999 (Oct. 1999).

Ji, J. et al. Strategy for qualitative and quantitative analysis in proteomics based on signature peptides. *J. Chromatography* 745, 197–210 (2000).

Kosaka, T. et al. Identification and C–Terminal Characterization of Proteins from Two–Dimensional Polyacrylamide Gels by a Combination of Isotopic Labeling and Nanoelectrospray Fourier Transform Ion Cyclotron Resonance Mass Spectormetry. *Anal. Chem.* 72, 1179–1185 (Mar. 15, 2000).

Kuster, B. & Mann, M. $^{18}$O–Labeling of N–Glycosylation Sites to Improve the Identification of Gel–Separated Glycoproteins Using Peptide Mass Mapping and Database Searching. *Anal. Chem.* 71, 1431–1440 (1999).

Leis, H.J. et al. Stable isotope labeled target compounds; Preparation and use as internal standards in quantitative mass spectrometry. *Curr. Org. Chem.* 2, 131–144 (1998).

Peptide fragmentation mechanism

Roepstorff - Fohlmann - Biemann - Nomenclatur

MALDI MS/MS spectrum (with pulsing) of a sample peptide

LABELING OF PROTEOMIC SAMPLES DURING PROTEOLYSIS FOR QUANTITATION AND SAMPLE MULTIPLEXING

RELATED APPLICATIONS

This application claims priority from U.S. Provisional patent application Ser. No. 60/210,496 filed Jun. 9, 2000 and U.S. Provisional patent application Ser. No. 60/293,664 filed May 25, 2001, both specifications of which are incorporated herein by reference.

BACKGROUND TO THE INVENTION

The large scale study of biological systems via the analysis of the protein complement, or 'proteomics', is increasingly dependent on the ability to rapidly screen complex mixtures of proteins in sensitive and efficient manners. As a result, the understanding of protein function in biological systems using large-scale proteomic approaches often pushes the limits of current analytical capabilities[1-5], in particular, that of protein separation and protein analysis by mass spectrometry. Arguably, the identification and quantification of a diverse array of protein expression represents the most significant challenge. Often conventional approaches such as two-dimensional poly acrylamide gels (2D-PAGE), even when coupled to mass spectrometry are limited in their utility for the identification and quantification of protein expression in samples.[6] Alternative approaches based on multidimensional chromatography coupled to mass spectrometry ('gel free approaches') have shown promising results; however, the lack of quantitation tools will also hamper the future of these approaches.[7-10]

Regardless of the platform employed, the identification of proteins usually relies on mass spectrometry based analysis. Over the years, matrix assisted laser desorption/ionization (MALDI)[11] and electrospray ionization[12] based mass spectrometers have come to dominate the field. In particular, the recently introduced orthogonal MALDI quadrupole time of flight mass spectrometer (QqTOF),[13-16] ESI ion trap mass spectrometers[17] and ESI quadrupole—quadrupole time of flight (QqTOF) mass spectrometers[18] have changed the approach to proteomics. As such, the challenges now lie in the preprocessing of samples (such as sample multiplexing and quantitative labeling) and post processing of the information (e.g. search algorithms and data-basing) rather than the nature of the ion-source.

The abilities to multiplex and to perform relative quantitation of protein samples are clearly not addressed by current proteomic technology. The needs are threefold: I) technology that allows for the differential labeling of protein samples so that their origin can be differentiated from other samples that have been mixed or pooled in the same sample, II) technology that can be used for rapid proteomic process prototyping, and II) technology that provides relative quantitation of protein levels based on mass spectrometric readout. For example, the differential isotopic labeling of samples produces distinct isotopic patterns that can be identified through mass spectrometric measurements. This would allow multiple samples to be run at one time while still maintaining sample tracking information. In addition, process development in proteomics has typically been constrained to the use of radioactive elements for quantitative assessment. Numerous parameters have been described in the literature to influence the success of MS based proteomic approaches. Therefore, the development of novel technology that can be routinely used to assess the efficiency of sample handling and processing steps is critical for the improvement of high throughput proteomic analysis processes. Furthermore, the development of relative quantitation technology based on the analysis of peptides by mass spectrometry is primordial to the rapid analysis of the analysis of the differential expression of proteins in different tissue samples (disease vs. normal), between different cell lines or differently stimulated cell lines.

SUMMARY OF THE INVENTION

In accordance with the present invention, there is first provided a sample tracking system that allows peptides analyzed by mass spectrometry to be identified with reference to the source of those peptides. Also in accordance with the present invention, there is second provided a sample quantitation system that allows the relative quantitation of peptides by mass spectrometry. With the aid of such a sample tracking system and sample quantitation system, peptides from various sources can be pooled and analyzed simultaneously, thereby increasing analytical throughput.

In general, both methods involve differential isotopic labeling of peptide or protein samples in order to identify the source of the sample, to permit multiplexing of samples during the sequencing step by mass spectroscopy, or to perform sample relative quantitation of proteins differently expressed in biological samples. The isotopes useful in the present invention are those that can be incorporated into a polypeptide chain or into groups that are attached to the sample peptide or protein as a consequence to post-translational modification. Preferably the isotope is a non-radioactive isotope, though radioactive isotopes can be used with appropriate safeguards. In certain preferred embodiments, the method utilizes isotopes of hydrogen, nitrogen, oxygen, carbon, phosphorous or sulfur.

According to one aspect of the invention, there is provided a method for encoding a plurality of polypeptide samples for analysis by mass spectrometry, comprising, for each individual sample:
  (i) cleaving the amide backbone of polypeptides in said sample to form sub-populations of fragments having carboxy-terminal residues;
  (ii) mass-modifying the carboxy-terminal residues of said fragments with one of at least two moieties of different molecular weight to produce a plurality of discrete populations of mass-modified fragments which differ in molecular weight by the addition of said moiety, wherein the moieties differ in molecular weight due to inclusion of isotypes of differing molecular weight,
  wherein, for each individual sample, the mass-modification produces the plurality of various discrete populations labeled, in a predetermined ratio of said at least two moieties, and which ratio is different from one of said individual samples to the next amongst the plurality of polypeptide samples.

According to one aspect of the invention, there is also provided a method for encoding a plurality of polypeptide samples for analysis by mass spectrometry, comprising, for each individual sample:
  (i) cleaving the amide backbone of polypeptides in said sample to form sub populations of fragments having carboxy-terminal lysine or arginine residues;
  (ii) mass-modifying the carboxy-terminal residues of a first portion of said fragments with a first moiety, and mass-modifying the carboxy-terminal residues of a second portion of said fragments with a second moiety, wherein the two moieties have different molecular weights, and the ratio between the first and second portions of said fragments are predetermined;

(iii) combining the two portions produced in (ii) and producing a plurality of discrete populations of mass-modified fragments which differ in molecular weight by the difference in molecular weight between the first and second moieties, wherein, for each individual sample, the mass-modification produces the various discrete populations reflecting said predetermined ratio, and which ratio is different from one of said individual samples to the next amongst the plurality of polypeptide samples.

In one embodiment of the invention, the moieties used can be halide, phosphate, amine, alkyl, thiol, or hydroxyl moieties, and are added by modification of the carboxyl groups generated by amide backbone cleavage, preferably added by modification of the amine group of the C-terminal lysine or arginine residue.

In one embodiment of the invention, the amide backbone cleavage can be achieved through enzymatic digestion, preferably includes treatment of the polypeptides with an enzyme which produces a carboxy terminal lysine and/or arginine residue, such as selected from the group of trypsin, Arg-C and Lys-C, or a combination thereof.

In one embodiment of the invention, cleavage of the amide backbone of the polypeptides and the mass modification can be carried out either in the same or separate reaction mixtures.

In one embodiment of the invention, polypeptide fragments can be separated based on size, solubility, electric charge and/or ligand specificity prior to ionization, using one or more procedures selected from the group of gel-filtration, isoelectric precipitation, electrophoresis, isoelectric focusing, ion exchange chromatography, affinity chromatography, and high performance liquid chromatography.

The instant invention also provides a method to analyze the molecular weights of polypeptide fragments by mass spectrometry, comprising:

(i) cleaving the amide backbone of polypeptides in said sample to form sub-populations of fragments having carboxy-terminal residues;

(ii) mass-modifying the carboxy-terminal residues of said fragments with one of at least two moieties of different molecular weight to produce a plurality of discrete populations of mass-modified fragments which differ in molecular weight by the addition of said moiety, wherein the moieties differ in molecular weight due to inclusion of isotypes of differing molecular weight, (iii) analyzing the molecular weights of said fragments by mass spectrometry.

In one embodiment, the mass spectrometry method used is selected from fast atomic bombardment (FAB), plasma desorption (PD), thermospray (TS), electrospray (ES) and matrix assisted laser desorption (MALDI).

The instant invention also provides a method for producing a peptide sample pool for analysis by mass spectrometry, the method comprising:

(i) forming a first peptide digest by hydrolyzing a first peptide sample in the presence of water containing a first volumetric ratio of two members of an isotope;

(ii) forming a second peptide digest by hydrolyzing a second peptide sample in the presence of water containing a second volumetric ratio of the said two members of an isotope, wherein said second volumetric ratio is different from said first volumetric ratio; and (iii) pooling the first peptide digest and the second peptide digest to form a peptide sample.

In one embodiment of the invention, each peptide digest is enzymatically hydrolyzed. In one prefered embodiment, the enzyme used for hydrolysis is trypsin. However, each peptide digest can also be carried out using chemical means other than enzymatic digestion.

In one prefered embodiment, the isotope used is selected from either $^{16}O:^{18}O$ pair or $^{2}H:^{1}H$ pair. And in a most prefered embodiment, the isotope used is $^{16}O:^{18}O$ pair.

In one embodiment of the invention, the volumetric ratio of $^{16}O:^{18}O$ differs by at least about 5%, preferably 15%, more preferably 30%, and most preferably 90% in terms of the amount of $^{18}O$ therein.

According to another aspect of the invention, there is provided a method useful to identify the source of peptides subjected as a peptide sample pool to analysis by mass spectrometry, the method comprising:

(i) obtaining a peptide sample pool comprising peptide digests formed by pooling protein digests from at least two different source proteins, wherein each source protein has been hydrolyzed in the presence of water containing an isotope ratio that is different for each protein sample;

(ii) subjecting the peptide sample to analysis by mass spectrometry to generate mass spectra comprising at least one signal doublet for each peptide in the sample, the signal doublet comprising a first signal and a second signal shifted a known units from the first signal, wherein said known units is the difference in molecular weight between the two members of said isotope;

(iii) determining a signal ratio for a given peptide by relating the difference in signal intensity or area between the first signal and the second signal;

(iv) correlating the signal ratio for the given peptide with the isotope ratio used to form the given peptide, thereby identifying the protein source of the given peptide.

According to another aspect of the invention, there is provided a peptide sample pool adapted to reveal the protein source of each peptide in the pool when the pool is analyzed by mass spectrometry, the pool comprising peptide digests formed by pooling protein digests from at least two different source proteins, wherein each source protein has been hydrolyzed in the presence of water containing an isotope ratio that is different for each protein sample.

In one prefered embodiment, the peptide sample pool is generated by labeling polypeptide samples using different volumetric ratios of $^{16}O:^{18}O$ in $H_2O$.

Another aspect of the invention provides a sofeware program for high throughput automated analysis of mass spectrometry data of peptide sample, comprising:

(i) identifying the peptides of interest in the sample with high probability based on their mass data;

(ii) generating a theoretical natural isotope abundance distribution based on said identification of (i);

(iii) subtracting the relative isotopic contribution by each of the labeled states and comapring them in a relative sense to generate the $^{16}O/^{18}O$ ration of interest.

According to another aspect of the instant invention, there is provided a method for quantitating the abundance of a given polypeptide present in a sample using mass spectrometry, comprising of:

(i) cleaving the amide backbone of polypeptides in said sample to form sub-populations of fragments having carboxy-terminal lysine or arginine residues;

(ii) cleaving the amide backbone of a standard sample of said given polypeptide to form sub-populations of fragments having carboxy-terminal lysine or arginine residues;

(iii) mass-modifying the carboxy-terminal residues of fragments generated in step (i) with a first moiety, and mass-modifying the carboxy-terminal residues of fragments generated in step (ii) with a second moiety, wherein the two moieties have different molecular weights;

(iv) combining the two portions produced in (iii), and subjecting the peptide sample to analysis by mass spectrometry to generate mass spectra comprising at least one signal doublet for each fragment, the signal doublet comprising a first signal and a second signal shifted a known units from the first signal, wherein said known units is the difference in molecular weight between the two said moieties;

(iii) determining a signal ratio for at least one fragment pair by relating the difference in signal intensity or area between the first signal and the second signal;

whereby the abundance of the given polypeptide is determined from the said signal ratio and the known amount of said standard sample of the given polypeptide, based on the principle that signal intensity is proportional to peptide abundance.

In one embodiment of the invention, the first and second moieties used are different isotypes of the same atom. In a most prefered embodiment, the isotypes used are $^{16}O$ and $^{18}O$ in $H_2O$.

In one embodiment of the invention, enzymatic digestion is used to cleave the amide backbone of the polypeptides. In a most prefered embodiment, the enzymatic digestion includes treatment of the polypeptides with an enzyme selected from the group of trypsin, Arg-C and Lys-C, or a combination thereof.

The key step of the disclosed method is the hydrolysis reaction to which each protein sample is subjected. The hydrolysis reaction yields peptides that incorporate either $^{16}O$ or $^{18}O$ in their carboxyl terminus. For all peptides formed from a given protein sample, the reaction thus yields two peptide species, one carrying carboxyl $^{18}O$ and one carrying only carboxyl $^{16}O$. However, the relative abundance of each peptide species within the sample is dictated by the $^{18}O:^{16}O$ ratio in the water used in the reaction, and the nature of the peptides formed. Thus, by using different relative amounts of $^{16}O$ and $^{18}O$ water to digest the different protein samples, the observed ratio of the corresponding $^{16}O$ and $^{18}O$ isotope profile for peptides becomes a quantitation tool, readily visible in mass spectra, that is useful to calculate the changes in protein expression level between different biological samples. In the simplest case, a protein standard of known quantity and digested in 95% $H_2^{18}O$ (labeled) is mixed with a sample of unknown concentration digested in natural abundance $H_2O$ (unlabeled). By comparing the relative intensities of the labeled to unlabeled peaks or peak areas, and knowing the standards concentration the relative concentration of the sample can be determined by the principle of isotope dilution.

The hydrolysis can be carried out using proteases with relatively high specificity, such as: trypsin or other serine proteases which produce carboxyl terminal Arg or Lys residues; cysteine proteases such as gingipains; endoproteinases such as Lys-C; or endopeptidases such as Arg-C.

In some instances, there can be complicated isotope distributions generated by the subject technique, and the correct isotope ratio can require some effort to derive from the spectra, particularly when using low level samples and/or when there is more than one site of isotopic incorporation in the protein. Furthermore, chemical noise in the spectrum can make quantitation difficult in some instances.

However, many of these difficulties can be overcome if the peptide/protein is fragmented, the ratio of isotopes, e.g., between $^{18}O$ and $^{16}O$, in the fragments is determined.

Amenable mass spectrometric formats for use in the invention include the ionization techniques such as matrix-assisted laser desorption (MALDI), continuous or pulsed electrospray (ESI) and related methods (e.g. Ionspray, Thermospray), or massive cluster impact (MCI); these ion sources can be matched with detection formats including linear or reflector time-of-flight (TOF), single or multiple quadrupole, single or multiple magnetic sector, Fourier transform ion cyclotron resonance (FTICR), ion trap, or combinations of these to give a hybrid detector (e.g. ion trap-time-of-flight). For ionization, numerous matrix/wavelength combinations (MALDI) or solvent combinations (ESI) can be employed.

We have also found, contrary to expectation, that the fragment method can work quite differently for MALDI versus electrospray methods. For instance, the "pulsing method" (see FIGS. 7 & 9) was used in both instances to boost a particular part of the spectrum. In the case of MALDI it is the so called Y1 ion at 175 and 177 Da, which is the C-terminal peptide fragment where the $^{18}O$ has been incorporated into Arginine (Trypsin generally produces peptides with Arginine or Lysine at the C-terminus, so approximately half of the peptide show the characteristic 177/175 pattern). This mass region of the fragment mass spectrum is substantially free of chemical noise. Even the noise that remains can usually be separated from the 175/177 Da pair using the high resolution of modern mass spectrometers such as the quadrupole time of flight instruments, for example. Up to 15 times increase in intensity can be achieved in MALDI using the "pulse method." In the case of ES/MS it is the mass region from about 400 to 800 Da which has abundant Y ion fragments, little isotopic complexity and little fragment background. Up to 6 times increase in intensity can be achieved in ES/MS using the "pulse method."

Another aspect of the invention relates to the economic use of the $^{18}O$ reagent. A potential limitation of the $^{18}O/^{16}O$ method for quantitation or encryption is the scarcity and price of the $^{18}O$ reagent that is generally produced as the byproduct of the radioactive creation of 19Flourine. We have discovered a method to decrease the consumption of $^{18}O$ by several orders of magnitude as follows: The protein mixture is first degraded by another enzyme or chemical entity, preferably the protease Lys-C that cleaves C-terminal to Lysine residues. We have found that this first step is advantageous to use in any case because Lys-C is a very aggressive and stable protease that works in highly denaturing conditions in which the protein mixture readily solubilized, such as 6 M Guanidine HCL. In a second step the peptides are adsorbed in a capillary or other small volume containers that reduce evaporation and can be cleaned by flushing liquid through it. The fact that the protein mixture has been reduced to a peptide mixture is particularly advantageous as peptides are easier to adsorb reversibly onto chromatographic material. In a preferred implementation, the peptide mixture is passed through a short capillary column containing a frit and C-18 chromatographic beads or other chromatographic peptide supports. The volume of the capillary section needs only to be large enough to hold chromatographic material sufficient for adsorbing the complex peptide mixture, typically in the range of 100 nL or so. The column is then flushed with clean buffer and subsequently with trypsin in $^{18}O$ digestion buffer.

Only small volumes of this buffer need be used as the column volume is extremely small. The buffer is chosen such that peptides are exchanged between liquid and solid phase, and are thereby accessible to trypsin. Digestion of peptides in the size produced by Lys-C is very rapid and efficient. (Beads with immobilized trypsin bound to them could make the procedure even more efficient.) Other advantages of performing the digestion at the peptide level in a small volume such as a capillary include the fact that there is very little evaporation from a capillary as well as very little exchange with atmospheric water. The peptides are now caused to flow out of the capillary into a system designed for mass spectrometric analysis. An example of this would be 'butt connecting' the short digestion column to a reversed phase column 'on-line' connected to a mass spectrometer, as commonly used for the analysis of complex peptide mixture. In this procedure, generally the same peptide will be produced as by a trypsin digestion alone, however, only the tryptic peptides with an arginines at the C-terminus may be have correct ratio of $^{18}O$ to $^{16}O$ corresponding to the makeup of the water in the buffer. (Trypsin may also cause incorporation of some $^{18}O$ into the C-termini previously created by Lys-C.) This may reduce the complexity of the mixture since only approximately half of the peptides—those ending in Arginine—would have a broad isotope distribution caused by $^{18}O$. It would not hamper quantification or encryption because there would still be many labeled tryptic peptides for each of the proteins. In summary, this two step method is as efficient or more efficient than trypsin digestion alone (and is therefore used even without the labeling step) but it allows incorporation of the isotopic label in a very small volume under more controlled conditions.

Although the following example lays out details of mass labeling with $^{16}O/^{18}O$ pair at the carboxyl terminal residues Lys or Arg generated by enzyme digestion, the instant invention is not limited to such specific modifications. For those skilled in the art it will be obvious that there are numerous possibilities, for introducing, in a predetermined manner, many different mass-modifing functionalities.

For instance, a simple mass modification can be achieved by substituting H for halogens like F, Cl, Br and/or I; or pseudohalogens such as NCN, SCN or NCS; or by using different alkyl, aryl or alkyl moieties such as methyl, ethyl, propyl, isopropyl, t-butyl, hexyl, phenyl, substituted phenyl, benzyl; or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another can be obtained by attaching homo- or heteropeptides through X to the carboxy or amino terminal residue of the peptide fragment. One example useful in generating mass-modified species with a mass increment of 57 is the attachment of oligoglycines, e.g. mass modifications of 74 (r=1, m=O), 131 (r=1, m=2), 188 (r=1, m=3), 245 (r=1, m=4) are achieved. Simple oligoamides also could be used, e.g. mass modifications of 74 (r=1, m=O), 88 (r=2, m=O), 102 (r=3, m=O), 116 (r=4, m=O) etc. are obtainable.

Finally, the labeling procedure can be carried out either in a common reaction mixture by using a predetermined ratio of the same moiety of different molecular weights (by virtue of including different isotopes), or in separate reactions by first labeling—with different moieties then mixing samples to different predetermined ratios.

These and other aspects of the present invention are now described with reference to the accompanying drawings, in which:

BRIEF REFERENCE TO THE DRAWINGS

FIG. 1. Positive mode MALDI QqTOF mass spectrum of the peptide fragment (YLYEIAR)H$^+$ present in the tryptic digest of BSA. Each mass spectrum was acquired under identical conditions, but each sample was generated using different buffer compositions. (A)~100% natural abundance water (i.e. $H_2^{16}O$), (B) 95% atom percent $H_2^{18}O$, (C) 1:1 mixture of 100% $H_2^{16}O$ and 95% atom percent $H_2^{18}O$. The peptide (YLYEIAR)H$^+$ is present at 500 fmol in (A) and (B) but because (C) is a mixture prepared after digestion it contains 250 fmol total from each sample (500 fmol total).

Figure 2:
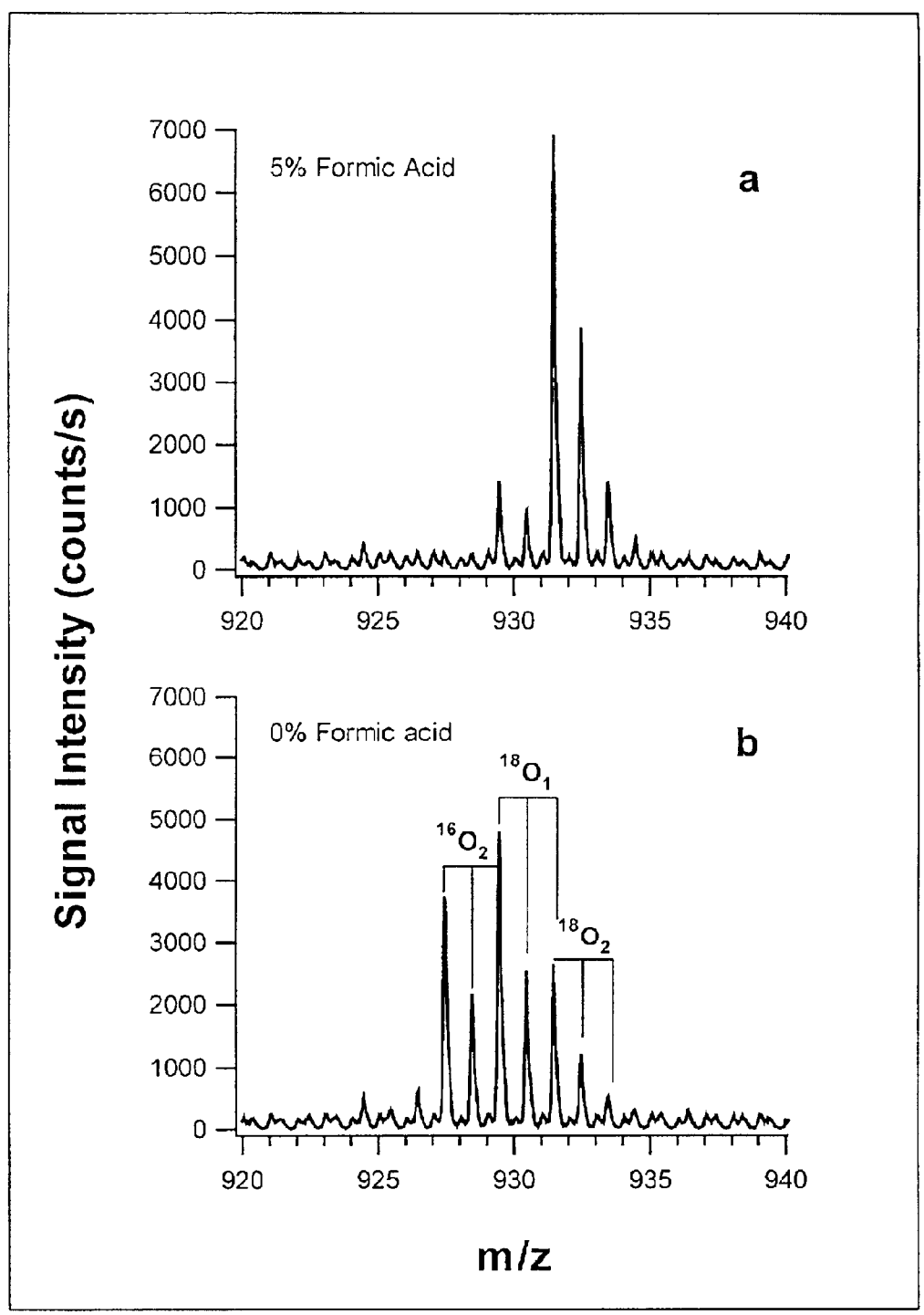

FIG. 2. Positive mode MALDI QqTOF mass spectrum of the peptide fragment (YLYEIAR)H$^+$ present in the tryptic digest of BSA performed in 95% $H_2^{18}O$. Each mass spectrum was acquired under identical conditions, but each sample was generated using different solution conditions. (A) The digestion was terminated by addition of 5% formic acid and diluted to 500 fmol/$\mu$L using natural abundance water. (B) The digestion was diluted to 500 fmol/$\mu$L using natural abundance water without the addition of formic acid. See FIG. 1 for species identification.

Figure 3:
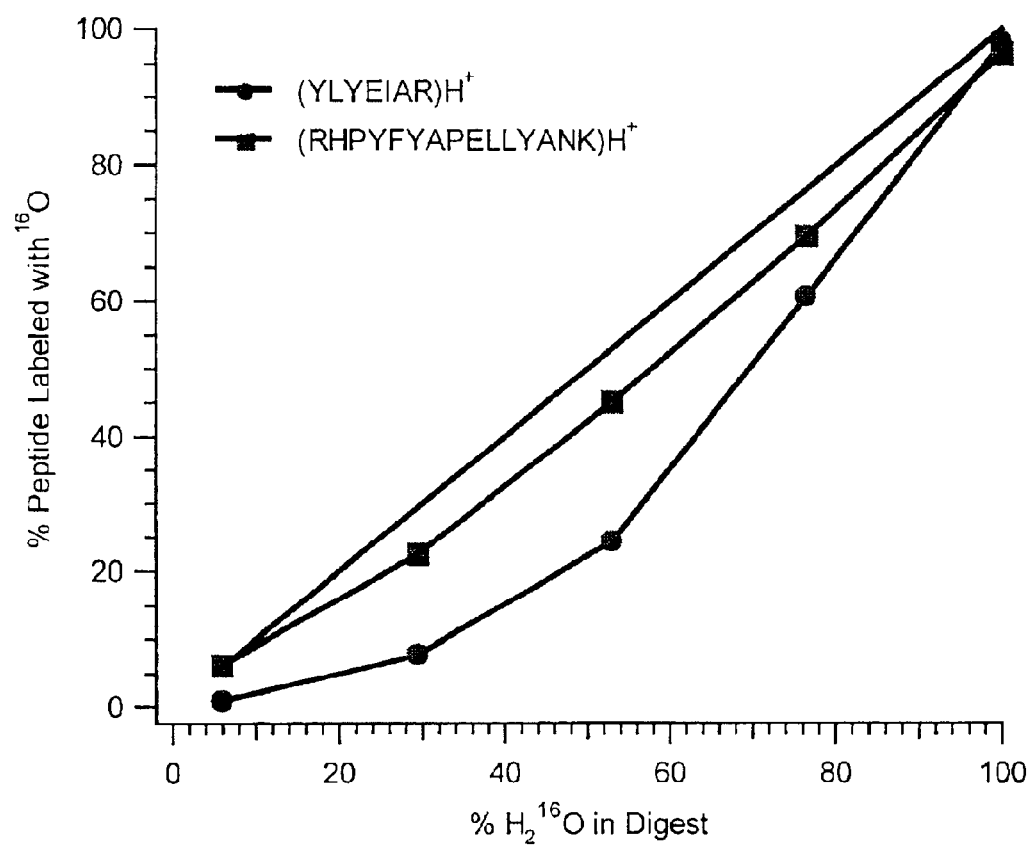

FIG. 3. The relationship between the formation of unlabeled peptide species and the % v/v content of $H_2^{16}O$ present in a BSA Tryptic digest buffer mixture containing a mixture of $H_2^{16}O$ and $H_2^{18}O$. The unlabeled peptide is expressed as a percentage of all of the labeled and unlabeled peptide species present. The straight line represents the distribution assuming that labeling was a 1:1 linear function of $^{16}O/^{18}O$ in the digest buffer content. The curved lower line represents a theoretical exchange curve where both terminal carboxyl oxygen atoms have equal probability of being exchanged with $^{18}O$.

Figure 4:
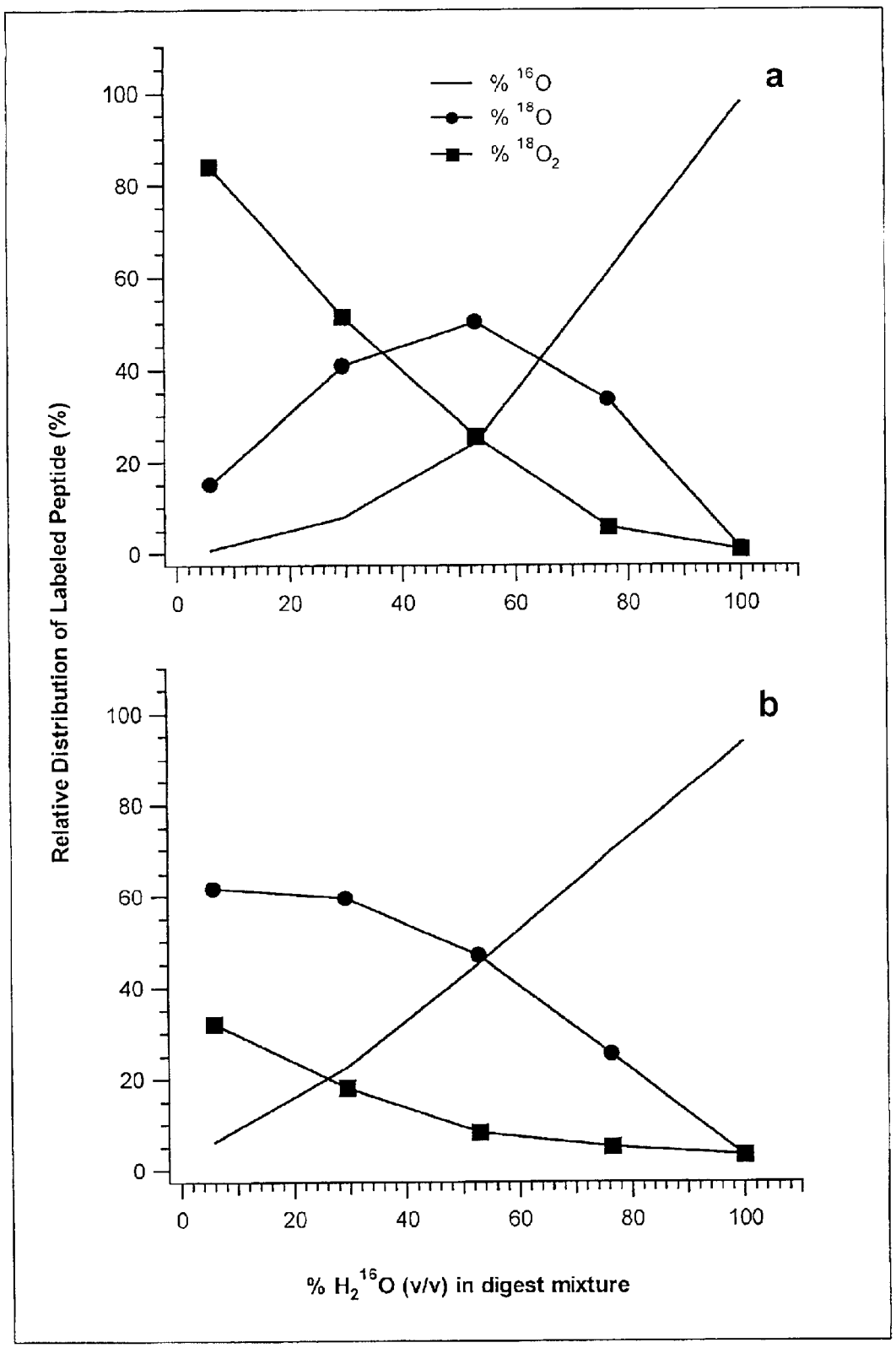

FIG. 4. The effect of the relative amount of $H_2^{16}O$ (% v/v) present in the BSA-Tryptic digest buffer mixture on the formation of unlabeled, singly labeled and doubly labeled peptide species. (A) for the peptide fragment YLYEIAR and (B) for the peptide fragment RHPYFYAPELLYyANK.

Figure 5:
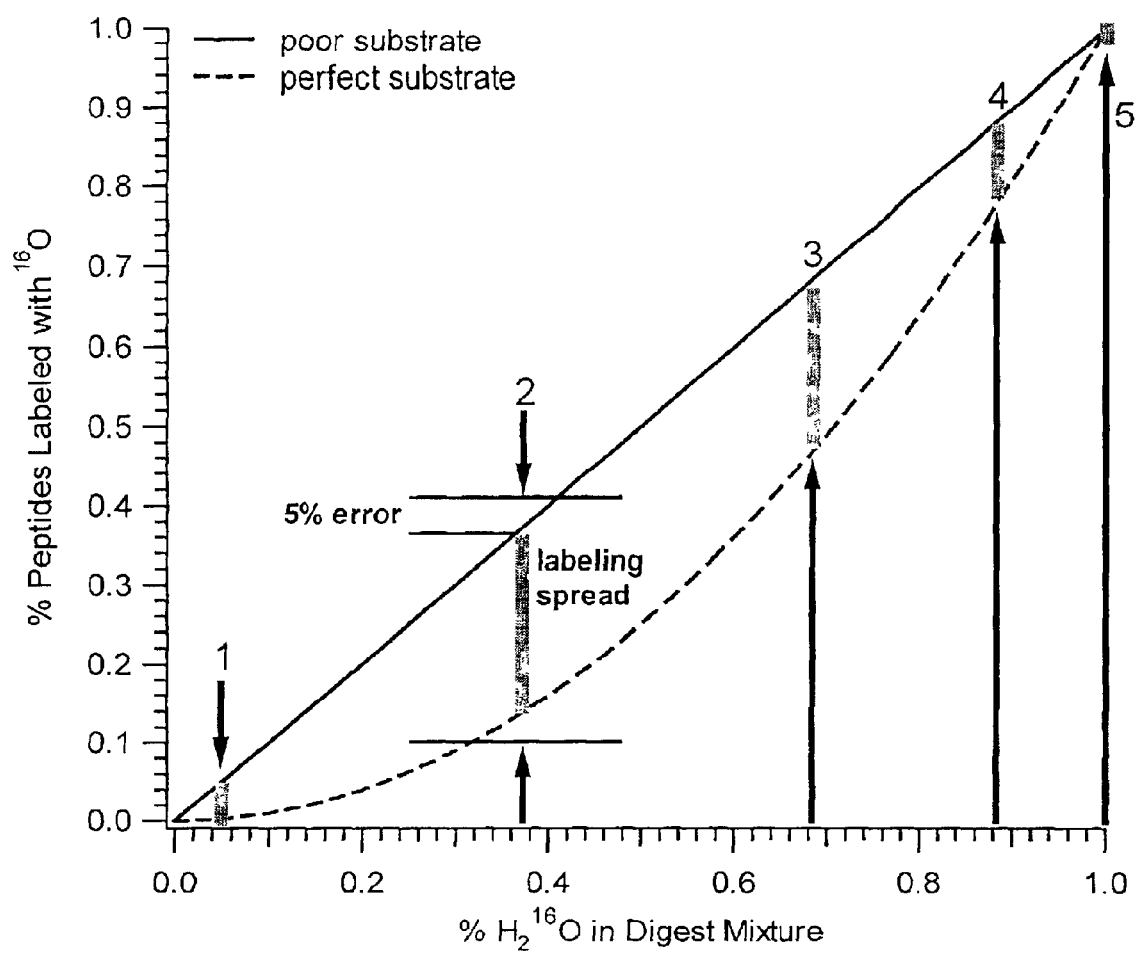

FIG. 5. Theoretical and Experimental Encryption Ratios. A) A plot defining the limits of relative peptide labeling based on the % $H_2^{16}O$ content present in a digestion mixture and the nature of the peptide substrate formed. The solid arrows identify five encryption regions. The corresponding labeling spread at each composition is high lighted by gray boxes, each box is bounded by an additional 5% error, giving a 10% gap between the possible labeling rations in any given encryption state. B) A plot of data from three different proteins digested in three different concentrations of $H_2^{18}O$ water and the corresponding experimental spreads.

Figure 6:
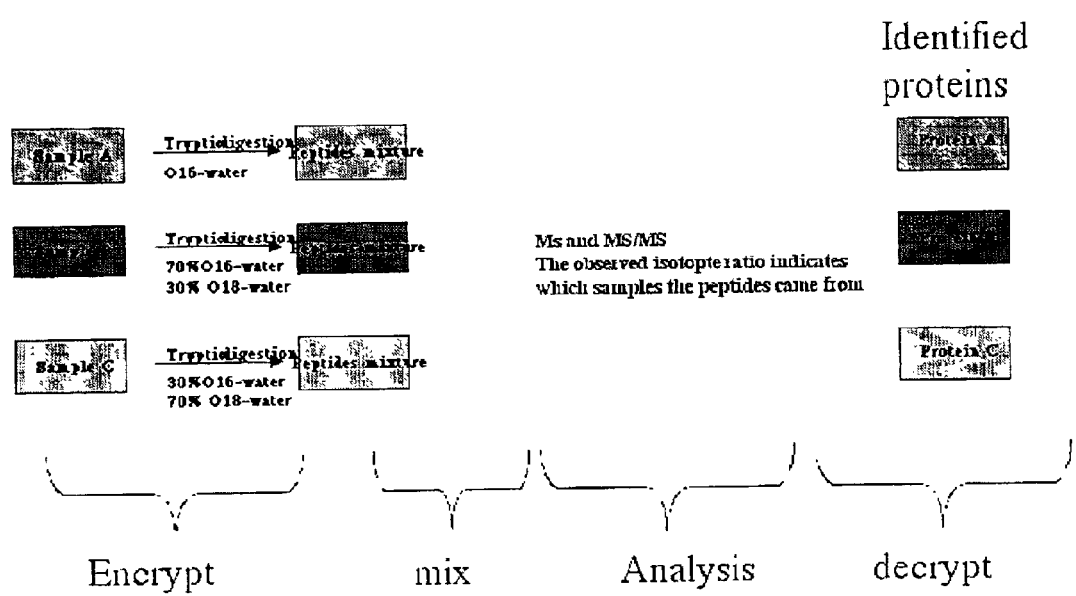

FIG. 6. A schematic view of an example of the process of the present invention.

Figure 7:
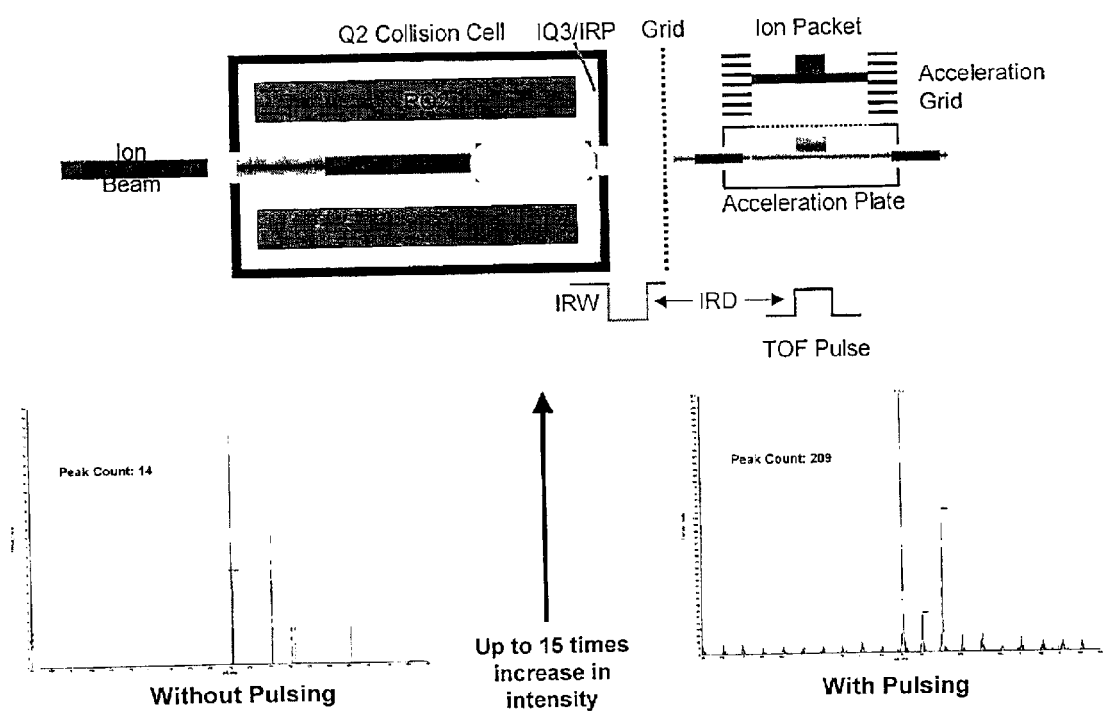

FIG. 7. Illustration of the QSTAR pulsing feature. Along with that two MS/MS spectra of the $^{18}O$ labeled 927.5 peak of BSA, the left acquired without pulsing and the right with pulsing resulting in a 15-time increase. The concentration of the BSA sample was approximately 25 $\mu$M/$\mu$L in solution, from which 1 $\mu$L was applied on the MALDI teflon target.

Figure 8:
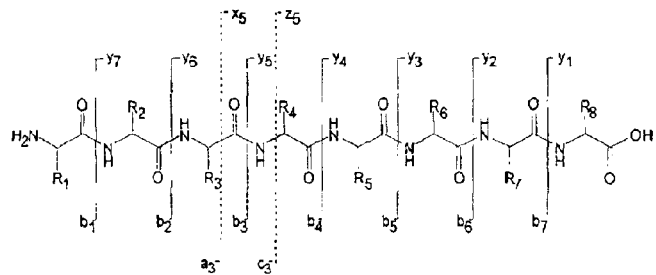

FIG. 8. Peptide fragmentation mechanism and the chemical origin of the various fragment ions. The C-terminal ions (right hand side) are of particular interest, either the very right hand side one (Y1 ion) in the case of MALDI or the middle ones in the case of electrospray.

Figure 9:
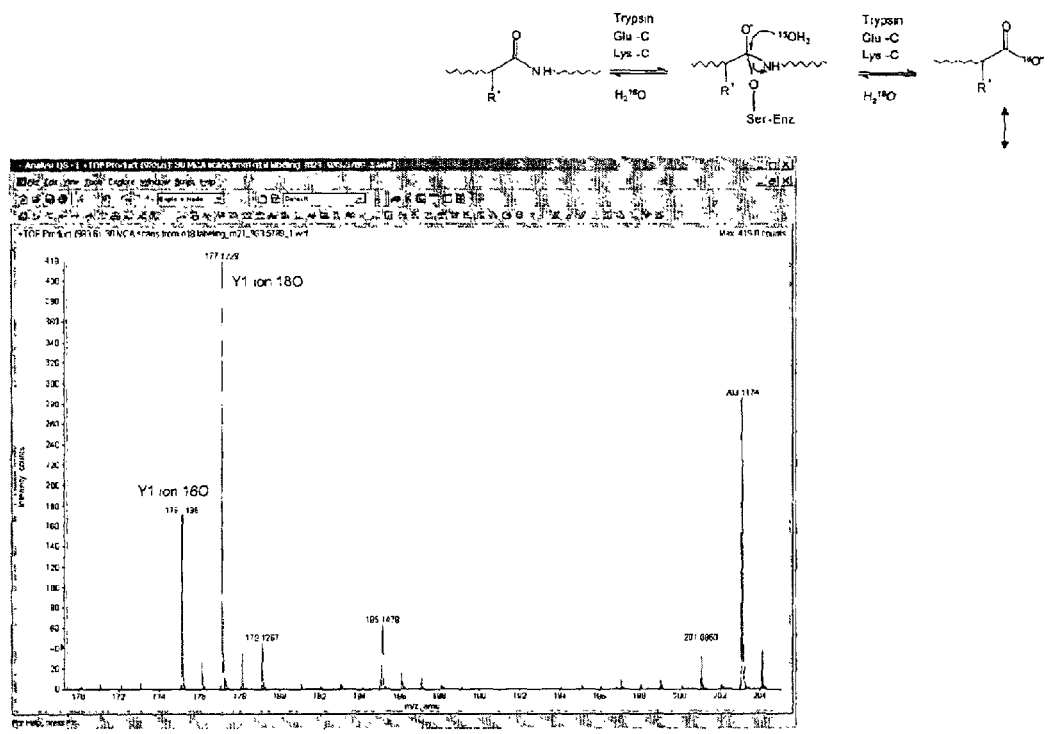

FIG. 9. MALDI MS/MS spectrum (with pulsing) of a sample peptide. The top part shows the reaction. The bottom part shows the lower mass part of an orthogonal MALDI MS/MS fragmentation spectrum. The feature to note is the 175 and 177 isotope pattern. First of all, a MALDI mass spectrum of a recombinant protein was acquired. The peptide peak at (M+H)+=933.579 was then selected in Q1 and fragmented in Q2. This gave rise to various fragments. What word is noticing is that the Y1 ion of tryptic peptides ending in arginine is always very prominent. Its mass is normally 175 Da. If the peptide has been $^{18}O$ labeled, the mass will now be 177. The ratio between peaks at 177 and 175 gives the ratio of the two protein states much more accurately than the ratio of the peptide isotope patterns. Pulsing technique as illustrated in FIG. 7 was used since without pulsing, the spectra would look worse and it would be more difficult to quantify the ratio of 175 to 177.

Figure 10:
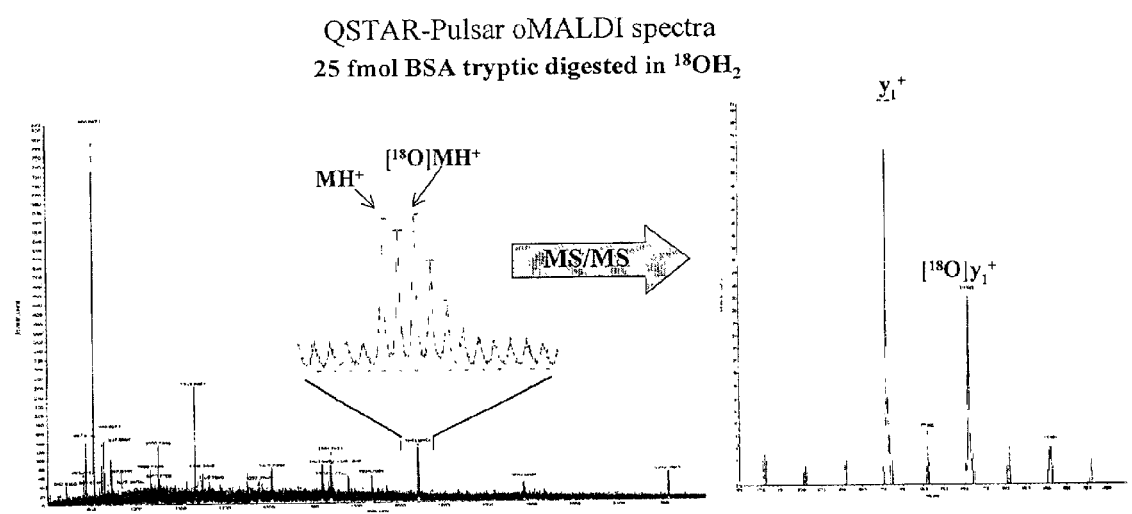

FIG. 10. Fragments are sometimes better than peptide ions for quantification. The reason is that there is a certain 'chemical noise' as well as interference from other peptides which make the correct isotope distribution difficult to discern. Additional factors that can skew the isotope distribution is deamidation which commonly occurs and which shifts part of the peptide population by one Da. This makes use of the $^{18}O$ method difficult in practice on the kind of low level samples that are interesting in discovery. However, when the peptide is isolated and fragmented in the mass spectrometer the ratio of 175 and 177 is quite easy to measure.

Figure 11:
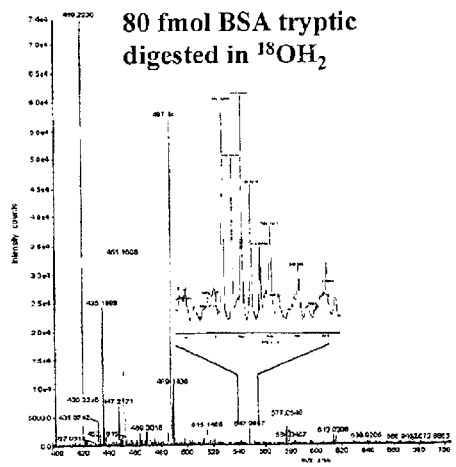

FIG. 11. An MS spectrum of 80 fmol BSA acquired using nanoESI QSTAR. The isotope cluster at mass to charge ratio (m/z) 548 is isolated and fragmented (shown to the right). The spectrum clearly show incorporation of the $^{18}O$, and the low mass MS/MS spectra can be used to calculate the relative ration between $^{16}O$ and 10, if the overlapping isotopic distributions are deconvoluted. The Y1 ion is not particularly abundant, so it cannot be used for quantification. Therefore, a stretch of C-terminal or fragment ion in the range from 400 to 800 Da, typically, were used for quantification. These ions have a very simple isotope distribution and each of the group of Y ions (and in fact all together) can be used to quantify. This again illustrates how much simpler it is to 'tease out' the correct quantification from the fragments compared to the parent ions.

DETAILED DESCRIPTION OF THE INVENTION AND ITS PREFERRED EMBODIMENTS

In addition to quantification, the use of isotope dilution incorporating $^{18}O$ labeling can be extended to diagnostic and encryption based applications to improve sample processing in proteomics. The labeling of peptides and the generation of stable standards is based upon enzymatic hydrolysis. The efficiency of labeling is therefore dependent on the activity of the enzyme (controlled by pH and time), the relative $H_2{}^{18}O$ content present in the digest buffer mixture in addition to the nature of the peptide products formed. Labeled standards appear stable and do not change appreciably under experimental conditions (pH 3–5) and over experimental time scales. A diagnostic evaluation of Ziptip preconcentration as a function of peptide concentration revealed that the relative recovery of peptides following preconcentration decreases as the absolute amount of peptides present in the original sample decreases. This suggests that at lower absolute amounts, Ziptip preconcentration may have only limited utility. It was also discovered that peptides are labeled in terms of spreads based on a probability function for a given relative composition of $H_2{}^{18}O$ in a digestion mixture rather than specific ratios. This reduces the absolute capability of $^{18}O$ labeling for use as an 'encryption' tool for the purpose of running multiple samples in tandem to reduce analysis time. In addition, the variability in labeling and the resultant complexity of isotopic envelopes would require very complex on-line computational methods to decode the sample mixture in order to fully realize the high throughput advantage of encryption. Finally, the large scale use of labeling ($^{18}O$, $^2H$, $^{15}N$, etc.) for the quantification of protein expression and encryption can be quite expensive on a 'per sample' basis and therefore may not be feasible.

In one embodiment, the present invention provides a technique for the labeling or "tagging" of protein digests prior to analysis by either electrospray ionization (ESI) or matrix assisted laser desorption ionization (MALDI) based mass spectrometers.

Typically, during the analysis of protein digests by mass spectrometry a mass spectrum (MS) is acquired to detect the mass to charge ratio (m/z) of the peptides. Then, the peptides are individually selected and fragmented generating tandem mass spectra (MS/MS) that are related to the amino acid sequence of the peptides. The protein is then identified either by searching the MSMS spectra against protein/DNA databases or by de novo sequencing of the peptides.

As shown in FIG. 6, in certain embodiments, the present approach uses $^{18}O$-labeled water and $^{16}O$ water to encrypt the protein digests during the enzymatic digestions. Each individual protein or each pool of proteins can be digested with a specific $^{18}O/^{16}O$ water ratio generating an isotopic pattern that can be recognized by mass spectrometers. A different $^{18}O/^{16}O$ water ratio is selected for every protein or protein pool. The encrypted protein digest samples can then be mixed prior to analysis by mass spectrometry. An isotopic pattern is observed for the peptides by the mass spectrometer and corresponds to the $^{18}O/^{16}O$ water ratio used during the digestion. Using this information each individual peptide can then be related to its original protein/protein pool.

Particularly, the present method utilizes in a first step the enzymatic digestion, typically fin using trypsin, of a first isolated protein or a protein pool. Protein isolation can be achieved using any routine technique, including SDS-PAGE or 2-D gel electrophoresis and the like. It is not essential for the present method that the protein preparation is pure; indeed the present method can be applied to impure preparations and to pools of source proteins. Accordingly, a "source protein" can be either a purified protein, an impure protein, or a mixture of proteins for instance from a given organism or from various organisms.

Key to the process is an enzymatic digestion that results in hydrolysis of the amide bond, to release a peptide incorporating a C-terminal carboxy group incorporating the mass label. The present process can accordingly be conducted using any enzyme that yields such carboxy groups. Conveniently and preferably, the process is performed using trypsin, given its well known enzymatic properties and given the mass spectra databases are focused at the identification of proteins in accordance with their tryptic digestion patterns. Alternatively, however, the process can also be applied using such enzymes useful to hydrolyze a protein, by the breaking of the amide bond. For instance, the invention can also be practiced using chymotrypsin, and the like.

To illustrate, the given sample is tagged, or labeled, by performing the source protein digestion in the presence of water made up of a given volumetric ratio of $^{16}O$ and $^{18}O$. Suitable volumetric ratios of $^{16}O:^{18}O$ range from 10:90 to 90:10. It can be useful to design as much separation in the chosen volumetric ratios as possible to simply the detection of the peptides within the mass spectra Thus, in the case where two protein samples are to be pooled for analysis following digestion, it will be useful to use water containing 10% $^{18}O$ to digest one protein sample, and to use water containing a much larger volume of $^{18}O$, say more than 50% and up to 90% to digest the other sample. As will be appreciated from the discussion that follows, this will allow for greater contrast in the doublet signal generated by the mass spec for each peptide. Alternatively, in the case where three protein sample digests are to be pooled, it will for instance be suitable to digest each protein sample in water containing 25%, 50% and 75% $^{18}O$, respectively. Considering normal experimental error, it is anticipated that up to 5 different (unique) encryption states can be readily used. Water containing the necessary blends of $^{18}O$ and $^{16}O$ can be produced readily by obtaining commercially available stock solutions of $^{18}O$ water (usually available at 95%) and then diluting with appropriate volumes of $^{16}O$ water optionally buffered with, for instance, ammonium bicarbonate.

Because pooled samples may contain the same protein from different sources, it can be useful to run separate controls with either pure $^{18}O$ and/or $^{16}O$ to generate spectra that can be used, by comparison with the experiment-derived spectra, to reveal such proteins.

Protein digestions can be performed in the usual manner, as prescribed for the chosen enzyme and in the presence of water containing the chosen blend of $^{16}O:^{18}O$. For instance, protein solutions of interest can be digested at slightly basic pH (8–9) in 100 mM ammonium bicarbonate at 37° C. overnight using trypsin. The digestion procedure can also includes steps for reduction, alkylation or other modification steps.

Another aspect of the invention relates to the economic use of the 18O reagent. A potential limitation of the 18O/16O method for quantitation or encryption is the scarcity and price of the 18O reagent which is generally produced as the byproduct of the radioactive creation of 19Flourine. We have discovered a method to decrease the consumption of 18O by several orders of magnitude as follows: The protein mixture is first degraded by another enzyme or chemical entity, preferably the protease Lys-C which cleaves C-termninal to Lysine residues. We have found that this first step is advantageous to use in any case because Lys-C is a very aggressive and stable protease which works in highly denaturing conditions in which the protein mixture readily solubilized, such as 6 M Guanidine HCL. In a second step the peptides are adsorbed in a capillary or other small volume which reduces evaporation and can be cleaned by flushing liquid through it. The fact that the protein mixture has been reduced to a peptide mixture is particularly advantageous as peptides are easier to adsorb reversibly onto chromatographic material. In a preferred implementation, the peptide mixture is passed through a short capillary column containing a frit and C-18 chromatographic beads or other chromatographic peptide supports. The volume of the capillary section needs only to be large enough to hold chromatographic material sufficient for adsorbing the complex peptide mixture, typically in the range of 100 nL or so. The column is then flushed with clean buffer and subsequently with trypsin in $^{18}O$ digestion buffer. Only small volumes of this buffer need to be used as the column volume is extremely small. The buffer is chosen such that peptides are exchanged between liquid and solid phase, and are thereby accessible to trypsin. Digestion of peptides in the size produced by Lys-C is very rapid and efficient. (Beads with immobilized trypsin bound to them could make the procedure even more efficient.) Other advantaged of performing the digestion at the peptide level in a small volume such as a capillary include the fact that there is very little evaporation from a capillary as well as very little exchange with atmospheric water. The peptides are now caused to flow out of the capillary into a system designed for mass spectrometric analysis. An example of this would be 'butt connecting' the short digestion column to a reversed phase column 'on-line' connected to a mass spectrometer, as commonly used for the analysis of complex peptide mixture. In this procedure, generally the same peptide will be produced as by a trypsin digestion alone, however, only the tryptic peptides with an arginines at the C-terminus may be have correct ratio of $^{18}O$ to $^{16}O$ corresponding to the makeup of the water in the buffer. (Trypsin may also cause incorporation of some $^{18}O$ into the C-termini previously created by Lys-C.) This may reduce the complexity of the mixture since only approximately half of the peptides —those ending in Arginine —would have a broad isotope distribution caused by $^{18}O$. It would not hamper quantification or encryption because there would still be many labeled tryptic peptides for each of the proteins. In summary, this two step method is as efficient or more efficient than trypsin digestion alone (and is therefore used even without the labeling step) but it allows incorporation of the isotopic label in a very small volume under more controlled conditions.

Peptide samples individually prepared from their source proteins, using water containing different volumetric amounts of $^{18}O$, can then be pooled and subjected to mass spectrometric analysis using well established instruments and techniques. The pooled sample can be subjected to analysis by MALDI. In this case, the pooled sample is desalted (e.g., using a ziptip(Millipore)) and applied with a MALDI matrix onto a MALDI plate. Once dried the plate is inserted into the vacuum chamber of a MALDI-TOF mass spectrometer (e.g., STR from Perceptive) and mass spectra are acquired for the plated samples. Similarly, the pooled peptides can be subjected to analysis by any other suitable mass spectrometer, including those appropriate for electrospray ionization or by on-line separation, ionization and detection using nanoLC.

The spectra generated by the analysis are then examined to identify individual peptides. In the spectrum, the peptides are revealed as signal doublets, in which the unlabeled signal is shifted by 2 mass units from a second signal (singly labeled, the difference in mass between $^{16}O$ and $^{18}O$, or by 4 mass units (doubly labeled, the difference in mass between $^{16}O$ and $^{18}O$. Each signal within the doublet appears with a different intensity, which indicates the abundance of the $^{18}O$ species of the peptide relative to the $^{16}O$ species of the peptide. By calculating either the signal area or the signal height (a less stringent measure) of one signal in the doublet, and relating that to the same metric for the other signal in the doublet, there is revealed a signal ratio for a given peptide that is consistent with the $^{16}O:^{18}O$ ratio used in its formation. Thus, the signal ratio for a given peptide correlates with the $^{16}O:^{18}O$ ratio to which the protein source of that peptide was subjected during digestion; Accordingly, the source of the peptide is revealed, and can be correlated. Such analysis can be achieved computationally using appropriately designed software. Alternatively, and provided the number of peptides in the pooled sample is not too large, the correlation can readily be done visually.

I. Sample encryption:

More particularly, and in accordance with one aspect of the present invention (i.e. sample encryption), there is provided a method for producing a peptide sample for analysis by mass spectrometry, the method comprising the steps of:

Forming a first peptide digest by enzymatically hydrolyzing a first protein sample in the presence of water containing a first volumetric ratio of $^{16}O:^{18}O$;

Forming a second peptide digest by enzymatically hydrolyzing a second protein sample in presence of water containing a second volumetric ratio of $^{16}O:^{18}O$ different from said first volumetric ratio; and Pooling the first peptide digest and the second peptide digest to form a peptide sample.

The key step of the disclosed method is the hydrolysis reaction to which each protein sample is subjected. The hydrolysis reaction yields peptides that incorporate either $^{16}O$ or $^{18}O$ in their carboxyl terminus. For all peptides formed from a given protein sample, the reaction thus yields two peptide species, one carrying a carboxyl $^{18}O$ at either or both of the terminal carboxyl oxygen atoms (labeled) and one carrying only carboxyl $^{16}O$ at both sites (unlabeled). However, the relative abundance of each peptide species within the sample is dictated by the $^{18}O:^{16}O$ ratio in the water used in the reaction, and the nature of the peptides formed. Thus, by using different relative amounts of $^{18}O$ to digest each protein sample, the abundance of $^{18}O$-bearing peptides becomes a tag, readily visible in mass spectra, that is useful to identify the source of peptides within the pool of tagged peptides.

The hydrolysis can be carried out using proteases with relatively high specificity, such as: try sin or other serine proteases which produce carboxyl terminal Arg or Lys residues; cysteine proteases such as gingipains; endoproteases such as Lys-C; or endopeptidases such as Arg-C.

More particularly, and in accordance with another aspect of the present invention, there is provided a method useful to identify the source of peptides subjected as a pool to analysis by mass spectrometry, the method comprising the steps of:

Obtaining a peptide sample comprising peptide digests formed by pooling protein digests from at least two different source proteins, wherein each source protein has been enzymatically hydrolyzed in the presence of water containing an $^{16}O:^{18}O$ ratio that is different for each protein sample;

Subjecting the peptide sample to analysis by mass spectrometry to generate mass spectra comprising a signal doublet for each peptide in the sample, the signal doublet comprising a first signal and a second signal shifted two mass units from the first signal;

Determining a signal ratio for a given peptide by relating the difference in signal intensity or area between the first signal and the second signal;

Correlating the signal ratio for the given peptide with the $^{16}O:^{18}O$ ratio used to form the given peptide, thereby identifying the protein source of the given peptide. Therefore, in this embodiment peptides are encoded during the proteolytic digestion of proteins. Different protein bathes can be encoded using different individual $^{16}O:^{18}O$ ratios, then mixed together and analyzed by mass spectrometry. The $^{16}O:^{18}O$ ratio observed for the peptides by mass spectrometry correlates to the different protein batches.

The digestion step and the mass-modification step can be performed either in a common reaction mixture or separately, the moieties used for mass-modification can be different isotypes of the same atom or different chemical moieties, and the mass-modification methods to achieve different labeling rations can be carried out either separately or in a common reaction mixture.

The fragments to be analyzed can be separated using any suitable means, including, but are not limited to gel-filtration, isoelectric precipitation, electrophoresis, isoelectric focusing, ion exchange chromatography, affinity, chromatography, and HPLC (high performance liquid chromatography).

II. Sample Quantitation:

According to another aspect of the instant invention, there is provided a method to quantitate samples using mass labeling coupled to mass spectrometry analysis. In one prefered embodiment of the invention, biological samples from at least two different states can be labeled and then compared. The states to be compared can be normal vs. diseased states, one diseased state vs. a different diseased state, samples obtained from the same source before and after certain treatments, or samples subjected to different kinds of treatments.

More particularly, and in accordance with a second aspect of the present invention (i.e. sample quantitation), there is provided a method for producing a peptide sample for analysis by mass spectrometry, the method comprising the steps of:

Forming a first peptide digest by enzymatically hydrolyzing a first protein sample or protein mixture in the presence of water containing a first volumetric ratio of $^{16}O:^{18}O$;

Forming a second peptide digest by enzymatically hydrolyzing a second protein sample in presence of water containing a second volumetric ratio of $^{16}O:^{18}O$ different from said first volumetric ratio; and Pooling the first peptide digest and the second peptide digest to form a peptide sample.

III. Exemplification

In meeting this need, the generation of isotopically labeled peptides as part of the digestion process has the potential to provide valuable quantification and diagnostic information. By combining peptide samples of unknown concentration with known concentrations of the same isotopically labeled peptide, isotope dilution analysis can be used to quantitate protein expression. Alternatively, equal amounts of labeled standards can be added to a variety of samples to assess the 'relative' expression level. Using these strategies, isotopically labeled standards can also be used as diagnostic tools to evaluate peptide recovery in proteomic process prototyping. Recently, significant attention has been focused on isotope-coded affinity tags (ICAT) reagents as tools for quantitative proteomics.[25-27] ICAT reagents are essentially affinity tags that contain linker chains with variable deuterium content (e.g. 0 or 8 deuterium) and a thiol (cysteine) specific reactive group. Comparing the intensity of a known concentration of isotope labeled peptide to that of an unlabeled peptide will therefore provide quantitative information. Although light ($D_0$) and heavy ($D_8$) ICAT reagents should in theory exhibit similar properties they often exhibit different retention times on chromatographic columns suggesting that they are not perfect isotope dilution standards. In similar approaches, Ji et al.[28] and Munchback et al.[29] have used deuterated biosynthetic derivitizing agents to label tryptic peptides. Both groups were able to identify and generate relative quantitative information on peptide samples. Other groups have incorporated 15N as part of a metabolic labeling strategy.[30]

The incorporation of $^{18}O$ into peptides is another stable isotope approach. $^{18}O$ is easily incorporated into peptides during digestion and/or through pH changes. Furthermore, the concentration of $^{18}O$ water can be brought up to 55 M to push the reaction towards completion even for low-level proteins. Early research[31,32] has demonstrated that $^{18}O$ can be incorporated into peptides through the enzyme-catalyzed incorporation of oxygen in the C-terminal carboxylic acids either after or as part of the digestion procedure. Different studies[33-35] have indicated that $^{18}O$ labeled amino acids could be generated via chemical hydrolysis reactions. These studies further demonstrated that back-exchange is minimized through control of solution conditions and, as such, $^{18}O$ labeled amino acids could be used as stable internal standards for isotope ratio analysis. Recently, researchers have used $^{18}O$ labeling to identify the peptide C-terminus for sequencing.[18,37] More recently, Schnolzer et al.[36] presented a comprehensive investigation of $^{18}O$ labeling specific to protease-catalyzed digestion of proteins. Later researchers have used $^{18}O$ labeling to track modifications[38] and MALDI-TOF analysis.[39]

Although much fundamental research has been focused on the development of 1O labeled peptides for quantitative standards, there has been relatively little reported on their use as diagnostic tools for proteomic process prototyping, or as part of a high throughput method for proteomics quantification. We describe how $^{18}O$ labeling, used as a diagnostic, can help refine sample-processing protocols. We also discuss the potential for $^{18}O$ labeling as part of an encryption based high-throughput strategy. By mixing samples digested using variable $H_2^{18}O/H_2^{16}O$ ratios in the digest buffer, peptides with unique isotope envelopes will be generated that can be used to define their origins (encryption). Processing data that contains samples with different encryption presents a unique challenge because not only does the isotope envelope change as a function of the relative $H_2^{18}O$ content in the digestion buffer, but also as a function of the peptide and its mass. A critical evaluation of the requirements for the rapid automated deconvolution of this data is presented. Furthermore, we describe how 60:80 water labeling can be used for the quantitation, by mass spectrometry, of the difference in protein expression levels between different biological samples.

Experimental Protocol

Instrumentation

All experiments were performed using a PE/SCIEX API QStar Pulsar with a MALDI experimental prototype source (PE/SCIEX, Toronto, Canada). This instrumental design has been A described in the literature.[13-16] Briefly, the sample and matrix solution were spotted onto a stainless steel 96 well plate in a 1:1 ratio and allowed to dry in a dust free environment prior to analysis. Each spot location is translated (x/y) and sampled relative to the laser focus on the plate via a Gravis 'game pad' using an external software program (V. Spicer, University of Manitoba, Winnipeg, Canada). A nitrogen laser (Laser Science Inc, VSL-337ND), operating at 337.1 nm, 20 Hz and with fluences between 50–150 $mJ/cm^2$, was used for all measurements. Sample spectra were acquired using the same basic instrumental operating conditions and acquisition times. In most cases these did not exceed 2 minutes per sample. Great care was taken to avoid detector saturation in order to ensure good isotopic abundance data quality.

Materials and Reagents

Bovine serum albumin (BSA, $\geq$99% Electrophoresis grade) was purchased from Sigma Chemical Company (St. Louis, Mo.) and was enzymatically digested in solution using sequencing grade porcine Trypsin (Promega, Madison, Wis.). The isotopically enriched water used for the preparation of all standard mixtures was 95% $^{18}O$ (Aldrich, Milwaukee Wis.). Milli-Q (Millipore, Bedford Mass.) natural abundance ($H_2^{16}O$) water was used for the preparation of all other samples. All solvents and chemicals used were HPLC grade (Fisher, Fairlawn, N.J., USA). Ziptip experiments were conducted using $\mu$-$C_{18}$ Ziptips (Millipore, Bedford, Mass.). MALDI matrix solutions were prepared by dissolving 30 mg of 2,5-hydroxybenzoic acid (DHB, Sigma, St. Louis, Mo.) in a 50/50 mixture of acetonitrile (ACN) and Milli-Q water containing 2% formic acid (FA, Superpure 98–100%, Merck KgaA, Dormstadt, Germany).

Labeling Procedure

Peptides are labeled during the tryptic digestion of proteins using solutions that contain specific ratios of $^{18}O/^{16}O$ labeled water. To minimize analytical errors during the diagnostic experiments, a concentrated protein stock solution (1 mL, 1000 pmol/$\mu$L) is first prepared in 100 mM $NH_4CO_3$ (ABC, pH 8.5) using natural abundance water. This stock solution has been reduced and alkylated with dithiothreitol (DTT) and iodoacetamide (OA), respectively, using typical procedures.[40] Aliquots (5 $\mu$L) of this stock solution are then diluted to 500 $\mu$L in 100 mM ABC in one solution prepared in natural abundance water and another in 95% $^{18}O$ enriched water. To these solutions a minimum volume of trypsin (1% v/v) dissolved in resuspension buffer (Promega) is added to give a 20:1 ratio of protein to enzyme. In this manner it is estimated that the total change in the $^{18}O/^{16}O$ ratio in the standard solution is 2%. The total concentration of protein digested is typically 10 pmol/=L. The digest solutions are then allowed to incubate from 4 to 12 hours at 37° C. Portions of each solution can then be removed and used for diagnostic experiments or frozen at –80° C. until needed.

Results and Discussion

Evaluation of Labeling Using Standard Proteins

The enzyme-catalyzed hydrolysis of peptide bonds during protein digestion provides a mechanism by which oxygen from the bulk solvent is introduced into the newly formed carboxy terminus. Early research has illustrated that there are two components to the exchange mechanism (e.g. see refs 31, 32, 36). Under normal conditions, the mechanism of Trypsin catalyzed cleavage involves the formation of an enzyme-peptide ester (acyl-enzyme intermediate) at the C-terminus that is subsequently hydrolyzed to form the free peptide. Once the free peptide is formed, it is thought that a back reaction can occur where the peptide-Trypsin ester complex is reformed and subsequently hydrolyzed. Rapid repetition of this process would result in exchange being possible at either or both of the C-terminal carboxyl oxygen atoms. The extent of $^{18}O$ labeling of the peptide is therefore a function of the relative $H_2^{18}O/H_2^{16}O$ ratio present in the buffer at this step, where the greater the $H_2^{18}O/H_2^{16}O$ ratio, the greater the probability that two $^{18}O$ atoms will be incorporated into the C-terminus. In accord, the incorporation of a second $^{18}O$ atom will also be dependent on the likelihood of the peptide fragment to be accepted as a pseudo-substrate ester intermediate and, as such, also be dependent on the nature of the peptide. If there are no differences in enzyme-substrate selectivity, then all peptides will be labeled with the same efficiency and degree under similar conditions after digestion.

Isotope Profile Distribution

The MALDI QqTOF data shown in FIG. 1 was acquired from a tryptic digest of BSA. It illustrates the relative isotopic distribution of the 161–167 peptide YLYEIAR acquired from buffer solutions containing 100% natural abundance $H_2O$ (FIG. 1a), 95% atom abundance $H_2^{18}O$ (FIG. 1b) and one prepared by mixing one part 95% atom abundance $H_2^{18}O$ digest and one part $H_2^{16}O$ digest (FIG. 1c). In FIG. 1a, the natural isotopic distribution calculated from the data 100%, 51.6%, 17.6%, 5.1%) is in strong agreement with the theoretical distribution predicted for the 161–167 peptide of 100%, 52.4%, 16.0% and 3.4% based on the elemental composition ($C_{44}H_{66}N_{10}O_{12}$). The data in FIG. 1b indicates that the sample digested in 95% $H_2^{18}O$ contains almost exclusively singly labeled (incorporation of one $^{18}O$) and doubly labeled (incorporation of two $^{18}O$) peptides. In this example the peptides are labeled with a relative ratio of 1:5 $^{18}O_1/^{18}O_2$. For the singly labeled peptide, the third and fourth peaks in its isotope envelope (m/z ~931.5 and ~932.5 respectively) would be obscured by overlap with the major peaks from the peptide containing two $^{18}O$ atoms. The relative signal intensity of the second (m/z ~930.5) peak to the first (m/z ~929.5) peak from the singly labeled peptide is 55% and in fair agreement with the theoretically expected value. Similarly, for the doubly labeled peptide, the ratio (52.3%) of the peak intensities of the second to first isotopes is also in close agreement with the theoretically expected value. Under these conditions the third and fourth peaks in the singly labeled peptide do not contribute significantly to the overall intensities of the first two masses of the doubly labeled peptide envelope. Clearly, these results demonstrate that $^{16}O:^{18}O$ water labeling is a valid approach either for the encodding of more than two different samples, as well as for the differential quantiration of protein expression levels in different biological samples.

Isotope Deconvolution for Quantitation

In contrast to ICAT experiments[25-27] the nature of $^{18}O$ labeling often results in isotopic overlap between labeled and unlabeled species as well as between two different labeling states (e.g. FIG. 1b). It is straightforward to deconvolute such data mathematically using isotope ratios.[39] Using this approach we have deconvoluted data acquired from a 50:50 mixture of 500 fmol YLYEIAR formed by digestion in natural abundance water and 500 fmol YLYEIAR formed by digestion in 95% $H_2^{18}O$. The relevant data from the MALDI mass spectrum acquired from this solution is given in FIG. 1c. The isotopic signature is based on contributions from both mixtures. The signal intensity of the peak at m/z 927.5 (3455 counts/s) can be used to evaluate the relative contributions of the other peaks at higher m/z in the $^{16}O$ digest isotopic envelope. Using the isotope ratios, the other significant peaks should have intensities of 1810 counts/s (m/z 928.5), 553 counts/s (m/z 929.5) and 104 counts/s (m/z 930.5). Within error, the peak at m/z 928.5 (1825 counts/s) agrees with the theoretical value exemplifying the usefulness of this method to provide good estimates of the relative contribution of each of the labeled species. Subtracting the calculated contribution (553 counts/s) from the $^{16}O$ digest solution from the peak at 929.5 (1157 counts/s) leaves ~604 counts/s due to the singly $^{18}O$ labeled peptide which means that only ~100 counts/s at m/z 931.5 is due to overlap with the singly labeled peptide (i.e. 2835 counts/s of the peak at m/z 931.5 is due to the doubly labeled peak). The ratio of $^{18}O_1/^{18}O_2$ in FIG. 1c can then be calculated as 604/2835 or ~1:5, in good agreement with what was observed in FIG. 1b. More importantly the total contribution of the peptide digested in natural abundance water to that in 95% $H_2^{18}O$ (i.e. $^{16}O/^{18}O$) can then be calculated as (3455 counts/s)/(604 counts/s+2835 counts/s) or 1.01 as expected for a 50:50 mixture. In general, the quality of this ratio will depend on the accuracy of sample handling steps and it assumes that the relative concentration of the peptide in labeled and unlabeled samples are the same. Errors as large as 10% can be expected based on the small sample volumes involved and there handling. The measurement precision based upon five replicates is typically 5% or better.

Evaluation of the Stability of the Labeling Process

When $^{18}O$ labeled species are used as internal standards it is important to understand the stability of these species and their general exchange characteristics in order to ensure the analytical accuracy. We have identified a set of parameters that can affect the stability of the labeling process and hence labeling efficiency. They are i) back exchange through hydrolysis, ii) effect of pH and iii) the nature of the peptide.

It should be noted that labeling efficiency (0–100%) in this context, refers to the degree to which a peptide is labeled, i.e. whether it is labeled with 0, 1 or 2 $^{18}O$ atoms. Labeling can be considered 100% if there remains no unlabeled peptides. The efficiency may be further differentiated between singly and doubly labeled peptides, where 100% double labeling (i.e. $^{18}O_2$) represents the maximum labeled state.

i) back exchange due to chemical hydrolysis. A series of experiments were conducted to clarify the significance of this process under standard conditions. In the first experiment, BSA was digested with Trypsin in natural abundance water for 24 hours. The digestion was then terminated and aliquots of the mixture were diluted to 500 fmol/μL in one solution containing Milli-Q water/5% FA (v/v) and a second one containing 95% $H_2^{18}O$/5% FA (v/v). Both sample solutions were then allowed to age for a further 24 hours in microcentrifuge tubes at 4° C. prior to analysis by positive ion MALDI MS. The results from the analysis are listed in Table 1 and indicate that no significant back exchange of labeled peptide occurs under the experimental conditions. In addition, no significant back exchange for all other detectable BSA peptide fragments was evident. For completeness, the reverse experiment where the protein was digested in 95% $H_2^{18}O$ and diluted in Milli-Q water also showed similar results. These results indicate that labeled peptide standards are stable under these conditions (5% FA) and over these time periods.

TABLE 1

The theoretical (natural abundance) and experimental isotope ratios[a,b] for the peptide YLYEIAR formed by the tryptic digestion of BSA in the presence of $H_2^{16}O$ and diluted as indicated[c].

| Mass (amu) | Theoretical Isotopic Ratios | Exp. Isotope Ratios Diluted in $H_2^{16}O^c$ | Exp. Isotope Ratios Diluted in $H_2^{18}O^c$ |
|---|---|---|---|
| 927 | 100 | 100 | 100 |
| 928 | 52.4 | 53.5 | 54.0 |
| 929 | 16.0 | 18.1 | 17.1 |
| 930 | 3.4 | 5.0 | 4.2 |
| 931 | 0.6 | 0.7 | 1.1 |
| 932 | 0.1 | 0.1 | 0.9 |
| 933 | 0.0 | 0.0 | 0.0 |
| 934 | 0.0 | 0.0 | 0.0 |
| 935 | 0.0 | 0.0 | 0.0 |

[a]n = 5, precision is better than 5%.
[b]Positive ion MALDI MS.
[c]The digest solution was diluted (10×) in $H_2^{16}O$/5% FA and $H_2^{18}O$/5% FA and allowed to mature for 24 hours at 4° C. prior to analysis.

ii) effect of formic acid. Formic acid is commonly used in the preparation and storage of protein/peptide solutions primarily to control the solution pH. The effect of formic acid concentration present in sample solutions (after digestion) on the stability of labeled species was therefore investigated. A control experiment was first run where BSA is digested in buffer mixtures containing 95% $H_2^{18}O$ overnight. Sample solutions (500 fmol/mL) are then prepared by diluting the stock sample solution in 95% $H_2^{18}O$ with formic acid ranging from 0–5% (v/v) and allowed to age for three hours at 4° C. prior to analysis. The results listed in Table 2 indicate that the labeling goes to completion (≧95%) in all cases. In addition, the peptide is labeled with the same relative % ratio of $^{18}O_1/^{18}O_2$ for all conditions. This indicates that for standards prepared in 95% $H_2^{18}O$ the labeling efficiency is not altered by the presence of formic acid, suggesting that the labeling efficiency has a stronger dependence on the enzyme, relative $H_2^{18}O$ content and time.

TABLE 2

The effect of % (v/v) formic acid on $^{18}$O labeling
efficiency for standards[a] prepared by digestion
in 95% $H_2$ $^{18}$O and dilution in 95% $H_2$ $^{18}$O[b].

| % Formic Acid (v/v) | $^{16}$O/$^{18}$O[c] Ratio | $^{16}$O/$^{18}$O Ratio (% RSD)[c] | $^{18}$O$_1$/$^{18}$O$_2$ Ratio (%)[b] | $^{18}$O$_1$/$^{18}$O$_2$ Ratio (% RSD)[c] |
|---|---|---|---|---|
| 5.0 | 0.0107 | 28.16 | 0.1749 | 6.75 |
| 2.0 | 0.0055 | 32.00 | 0.1719 | 3.78 |
| 1.0 | 0.0091 | 42.40 | 0.1734 | 3.91 |
| 0.1 | 0.0092 | 73.26 | 0.1391 | 5.99 |
| 0.0 | 1.0017 | 20.25 | 0.1724 | 3.25 |

[a]Positive ion MALDI MS of YLYEIAR.
[b]The digested solution was diluted and allowed to age for 3 hours at 4° C. prior to analysis.
[c] $^{18}$O = ($^{18}$O$_1$ + $^{18}$O$_2$).
[d]n = 5.

The reverse experiment was then conducted in exactly the same procedure as that described above. The difference, however, being that the $^{18}$O-labeled standards in the digest mixture are diluted in Milli-Q water containing formic acid ranging from 0–5% (v/v). The data listed in Table 3 are different than that in Table 2; they indicate that when a digest mixture containing $^8$O-labeled peptide, is diluted in Milli-Q water, the amount of formic acid influences the labeling efficiency. FA (or any acid) is usually added to reduce the pH and stop the digestion by inhibiting Trypsin activity. Consistent with earlier research [36], the data indicates that under high pH (low % v/v FA) the enzyme is still active and continues to catalyze the back exchange in the medium that contains predominantly $^{16}$O (Milli-Q water). An example of this is clearly illustrated in FIG. 2, where the positive ion MALDI mass spectrum was acquired from samples diluted in 5% FA and 0% FA. Under acidic conditions (pH 3–4, 2–5% FA) no significant back exchange was observed over periods of several days. Samples frozen at −20° C. for several months exhibited slightly more back exchange. A significant conclusion from these experiments is that samples can be diluted in natural abundance water containing 1–5% FA (pH<4) without significant modification of the labeling over the course of an analysis and, as such, preserve expensive 95% $H_2$$^{18}$O stock solutions. In addition it also highlights the effect of pH on the enzymes activity and hence the labeling efficiency.

TABLE 3

The effect of % (v/v) formic acid on $^{18}$O labeling
efficiency for standards[a] prepared by digestion in
95% $H_2$ $^{18}$O and dilution natural abundance $H_2$O[b].

| % Formic Acid (v/v) | $^{16}$O/$^{18}$O Ratio[c] (Average)[d] | $^{16}$O/$^{18}$O Ratio[c] (% RSD)[d] | $^{18}$O$_1$/$^{18}$O$_2$ Ratio[c] (Average)[d] | $^{18}$O$_1$/$^{18}$O$_2$ Ratio[c] (% RSD)[d] |
|---|---|---|---|---|
| 5.0 | 0.016 | 15.83 | 0.245 | 3.54 |
| 2.0 | 0.026 | 7.98 | 0.222 | 4.72 |
| 1.0 | 0.022 | 5.00 | 0.200 | 7.65 |
| 0.1 | 0.148 | 3.56 | 0.742 | 2.90 |
| 0.0 | 1.326 | 2.30 | 5.468 | 13.15 |

[a]Positive ion MALDI MS of YLYEIAR.
[b]The diluted solution was diluted and allowed to age for 3 hours at 4° C. prior to analysis.
[c] $^{18}$O = ($^{18}$O$_1$ + $^{18}$O$_2$).
[d]n = 5.

iii) nature of the peptides. In addition to parameters such as pH, $H_2$$^{18}$O content, digestion conditions and time, the labeling efficiency can depend on the nature of the peptide. The data presented in Table 4 lists the relative labeling efficiency (labeled to non-labeled) and relative degree of labeling for a series of peptide fragments. In all cases reported so far, the labeling efficiency (in 95% $H_2$$^{18}$O) is close to 100% where typically only <5% of the peptide exists in an unlabeled state and is consistent with the enzyme-catalyzed hydrolysis of the protein. On the other hand, the relative degree of labeling was less consistent. The majority of peptides were doubly labeled having $^{18}$O$_1$/$^{18}$O$_2$ ratios on the order of 0.2. For other peptides this ratio was reversed being primarily singly labeled.

TABLE 4

The relative labeling efficiency of peptides formed
by the tryptic digestion of BSA in the presence of $H_2$ $^{18}$O[c].

| Peptide | $M_R$ (amu) | $^{16}$O/$^{18}$O Experimental Ratio (Average)[a, b] | $^{18}$O$_1$/$^{18}$O$_2$ Experimental Ratio (Average)[a, b] |
|---|---|---|---|
| YLYEIAR | 926.49 | <0.10 | 0.20 |
| FKDLGEEHFK | 1248.61 | <0.10 | 1.00 |
| HLVDEPQNLIK | 1304.71 | <0.10 | 1.05 |
| YICDNQDTISS[c] | 1442.63 | <0.10 | 0.20 |
| TCVADESHAGCEK[c] | 1462.58 | <0.10 | 0.21 |
| LGEYGFQNALIVR | 1478.79 | <0.10 | 0.17 |
| DAFLGSFLYEYSR | 1566.74 | <0.10 | 0.19 |
| KVPQVSTPTLVEVSR | 1638.93 | <0.10 | 0.19 |
| HPYFYAPELLYYANK | 1887.92 | <0.10 | 3.70 |
| RHPYFYAPELLYYANK | 2044.02 | <0.10 | 3.00 |

[a]n = 5, precision is better than 5%.
[b]Positive ion MALDI MS.
[c]modified with iodoacetamide.

A number of researchers have already noted that the degree of labeling was dependent on the nature of the peptide. In particular, Schnolzer et al.[36] have observed that smaller peptides (e.g. tripeptides) were less likely to be doubly labeled, presumably because they formed poorer pseudo-substrates with trypsin and therefore, are not involved in the back reaction to an appreciable degree. Other researchers have also shown that the degree of exchange depends on the enzyme substrate specificity.[31,32] As such, certain peptide fragments formed during the initial enzyme catalyzed hydrolysis may make poor pseudo-substrates in the back reaction and therefore, have very slow secondary exchange rates. Although labeling is not universally consistent from peptide to peptide, all of the detectable peptides were labeled. Peptides of different physical characteristics (e.g. hydrophobicity, phosphorylation, etc.) can then be selected and used to evaluate the impact of various test systems and/or protocols on their specific recovery.

Application of $^{16}$O/$^{18}$O Isotope Ratios for Proteomic Prototyping

The use of $^{16}$O/$^{18}$O isotope ratios represents a generic yet effective approach to evaluating and refining many proteomic processes. Here we present an evaluation of one of the many common sample-processing steps in proteomics, the ZipTips purification of peptides. ZipTip pipette tips are often used to concentrate and purify peptide digest mixtures prior to analysis by mass spectrometry in an effort to improve data quality. The $\mu_{C18}$-ZipTip is a 10 $\mu$l polypropylene pipette tip variant that contains a bead (~0.2 $\mu$L) of $C_{18}$ resin. Essentially, the tip is operated as a micro extraction column. The ZipTip procedure can be done in a manual or automated manner and is used for both MALDI and nanoES sample preparation. Basic descriptions of some preconcentration protocols are available in the literature[24] and specifically for the $\mu_{C18}$-ZipTip in the Users Guide provided by Millipore.

We are interested in obtaining a better understanding of the relative loss of sample that occurs during the $\mu_{C18}$-ZipTip purification and preconcentration step in an effort to better tailor our sample handling for proteomics. To evaluate this we investigated peptide recovery from a BSA digest using labeled ($^{18}$O) and unlabeled ($^{16}$O) standards and standard protocols. Known quantities of unlabeled sample were preconcentrated using the $\mu_{18}$-Ziptip procedure. To the recovered sample, the same absolute amount of labeled peptide was added. If no loss of the unlabeled peptide occurs, then the labeled and unlabeled peptides should be present in the final solution in equal amounts (1:1 ratio). As a control, 1:1 mixtures of the labeled and unlabeled peptide standard mixtures were prepared without ZipTips and analyzed at the same time as the experimental samples. In this manner any corrections based on differences in concentration of the labeled and unlabeled standard mixtures can be made. Samples containing 1000, 500, 200, 100 and 50 fmol absolute amounts of a BSA digestion mixture were investigated and the results presented in Table 5. The same Ziptip procedure was used for all samples and five individual replicates were run for each concentration. From the data a number of interesting features are apparent. At absolute loadings of 500 and 1000 fmol only a 70% recovery was achieved corresponding to 30% relative loss of sample. As the absolute amount was decreased the relative recovery decreased and therefore the absolute loss increased. At 50 fmol, the absolute recovery could only be estimated because of the poor signal to noise ratio of the sample compared with the standard. From this data it appears that the relative recovery of peptides decreases with concentration when $\mu_{C18}$-ZipTip procedures are employed. In all cases the singly labeled to doubly labeled peptide ratio ($^{18}O_1/^{18}O_2$) was monitored to ensure that the standard was giving consistent ratios (Table 5). Similar results were obtained for other peptides.

TABLE 5

Sample loss during $\mu$C18-ZipTip purification and preconcentration as a function of absolute protein digest loading.

| Abs. BSA (fmol) | $^{16}O/^{18}O$ Ratio (Average)[a, b, c] | $^{16}O/^{18}O$ Ratio (% RSD)[a, b, c] | $^{18}O_1/^{18}O_2$ Ratio (Average)[a, c] | Sample Loss (%) |
|---|---|---|---|---|
| 1000 | 0.70 | 4.70 | 0.16 | 30 |
| 500 | 0.72 | 11.82 | 0.16 | 28 |
| 200 | 0.48 | 20.90 | 0.15 | 50 |
| 100 | 0.14 | 36.12 | 0.14 | 86 |
| 50 | ≦0.10 | NA | 0.16 | ≧90 |

[a] Positive ion MALDI MS of YLYEIAR.
[b] $^{18}O = (^{18}O_1 + {}^{18}O_2)$.
[c] n = 5

During the $\mu_{C18}$-ZipTip procedure peptide losses could occur during the binding step, wash step, elution step or during normal sample handling. An evaluation of the residual solutions from the initial binding and wash for the higher level samples indicated that the majority of the sample was lost during the initial binding step, with less than 10% coming off in the wash. A thorough investigation of the relative recovery as a function of the nature of the peptide has not been conducted.

A second interesting feature of the data is that significant variation in sample recovery exists at each concentration. It is estimated that when suitable procedures are employed that the major source of variation is operator dependent and that possible inconsistencies in $\mu_{C18}$-ZipTip manufacturing is a lesser problem. As such, although the data in Table 5 represents a typical set and the trends have been verified with duplicate experiments it should be stressed that the absolute recoveries at these levels may vary and that recoveries may be dependent on the nature of the peptide. In some cases recoveries in the range of 80–90% have been observed, in others the recoveries have been lower.

Application of $^{16}O/^{18}O$ for Sample Encryption

The ability to analyze more than one sample simultaneously presents an attractive approach to improving sample throughput. For high throughput environments it becomes critical. The specific labeling of peptides in a controlled manner presents the possibility for sample encryption and therefore a unique approach to standard 'high throughput' methods. In theory, sample can be 'encoded' during the encryption step by controlling the relative composition of the digest buffer $H_2^{16}O/H_2^{18}O$ ratio and then decoded after analysis by examining the relative isotopic envelope of each peptide fragment. For example, consider the case where one sample digested in $H_2^{16}O$, one in $50/50H_2^{16}O/H_2^{18}O$ and one in 95% $H_2^{18}O$ are mixed together and analyzed concurrently in the same experiment. Peptides digested in $H_2^{16}O$ will have the normal isotopic distribution, the one digested in $50/50H_2^{16}O/H_2^{18}O$ will have an isotopic distribution that approximates a 1:1 $^{16}O/^{18}O$ ratio for each peptide and the one digested in 95% $H_2^{18}O$ will have an isotopic envelope that is shifted by 24 Daltons depending on the peptide and its labeling efficiency. By varying the content of the $H_2^{16}O$ in buffer mixtures to ratios of, for example, 100%, 75%, 50%, 25% and 5% (v/v) relative to $H_2^{18}O$, theoretically one could combine and analyze five unique samples at once and thus multiply the number of analyses per unit time accordingly. In order to properly assess the possibility for sample encryption, the ability to selectively label peptides in a controlled manner and with specific ratios must first be verified.

Labeling efficiency at different encryption ratios. The first step in evaluating the encryption process is to determine the labeling efficiency at a number of different $H_2^{16}O/H_2^{18}O$ solution compositions. FIG. 3 illustrates the relative composition (%) of just the $^{16}O$ labeled peptides as a function of the relative content (% v/v) of $H_2^{16}O$ in a $H_2^{16}O/H_2^{18}O$ digestion buffer mixture. The two peptide fragments YLYEIAR and RHPYFYAPELLYYANK were selected for this illustration because of their different relative labeling efficiencies (see Table 4). Neither peptide is labeled in a manner directly proportional to relative % (v/v) content of $H_2^{16}O$ as defined by the straight line in FIG. 3a The peptide YLYEIAR deviates significantly from the theoretical curve whereas the larger peptide RHPYFYAPELLYYANK deviates to a much lesser degree. In general, peptides with larger $^{18}O_1/^{18}O_2$ ratios (Table 4) more closely resemble the theoretical labeling ratio whereas those with smaller $^{18}O_1/^{18}O_2$ ratios deviate to a larger extent.

It is important to be able to understand why peptides exhibit different labeling efficiencies in the presence of different digest buffer compositions (i.e. $H_2^{16}O/H_2^{18}O$) to fully realize the potential for encryption. One possible reason is that the newly formed peptide fragments react poorly in the back reaction and reform peptide-enzyme complexes at an appreciable rate. In such cases, a second exchange may be very slow or non-existent during normal digestion periods. Labeling will therefore be restricted to a single exchange (one $^{18}O$ atom) occurring at the time of the initial peptide bond cleavage, and the relative extent of the labeling will be linearly (1:1) dependent on the digest buffer composition (i.e. $H_2^{16}O/H_2^{18}O$, as given by the straight line in FIG. 3a). For peptides that serve as better substrates, the probability of the peptide acquiring two $^{18}O$ atoms increases. In the presence of excess $H_2^{18}O$ the ratio of labeled to non-labeled peptides increases further. This behavior is illustrated in FIG. 4a where the relative concentration of the doubly labeled species is only significant at low ratios of $H_2^{16}O/H_2^{18}O$ and decreases rapidly as the ratio is increased.

If the peptide is considered a good substrate in its back reaction with trypsin, a singly labeled peptide will therefore have an equal probability of exchanging an oxygen atom making it either unlabeled ($^{16}O$ solvent exchange) or doubly labeled ($^{18}O$ solvent exchange) in 50/50 mixtures of $H_2^{16}O/H_2^{18}O$. If we consider that initially there is a rapid equilibration of the unlabeled peptide in $50/50 H_2^{16}O/H_2^{18}O$, giving roughly a 50/50 ratio of singly labeled to unlabeled peptide, then the remaining 50% unlabeled can be further exchanged. If $^{16}O$ from the solvent exchanges with $^{18}O$ at the terminal carboxyl group then the peptide becomes unlabeled, if $^{16}O$ exchanges with $^{16}O$ then nothing changes. Similarly, if $^{18}O$ from the solvent exchanges with $^{16}O$ then the peptide becomes doubly labeled, and if $^{18}O$ exchanges with $^{18}O$ then nothing changes. Ignoring any kinetic isotope effects, the probability to form unlabeled and doubly labeled peptides from a singly labeled species (~50% of peptides) should be equal and therefore each should exist at equal but at lower relative concentrations than the singly labeled species (i.e. each at ~25%). Therefore the relative composition of unlabeled to singly-labeled to doubly-labeled peptides in a 50:50 mixture of $H_2^{16}O/H_2^{18}O$ might be expected to be 1:2:1. In this case the relative content of unlabeled peptide is only 1 part in 4 or ~25%. Labeling is therefore not strictly a linear function of the relative buffer composition. For $H_2^{16}O/H_2^{18}O$ ratios that favor $H_2^{18}O$ the equilibrium will be skewed in favor of the total labeled species content vs. the unlabeled species and vice versa. To a first approximation this sort of behavior is illustrated in FIG. 4a, where because there are two probable labeled states vs. only one unlabeled state, the unlabeled state does not exceed 50% until the $H_2^{16}O/H_2^{18}O$ ratios approach 75%, however, for the poorer substrate (FIG. 4b) the unlabeled state follows a more linear relationship.

Accepting the above argument, a model can be developed to better define the boundary of the labeling efficiency of proteins based on their character and the relative $H_2^{18}O$ content in the digest mixture. Let us assume that the digest buffer is comprised of $p*100\%$ $H_2^{16}O$, and $(1-p)*100\%$ $H_2^{18}O$ (note that $(p+(1-p))=1$). In this manner p is defined to be the probability that any given water molecule is $H_2^{16}O$, and 1–p the probability that it is $H_2^{18}O$. Therefore p is related to the probability that a 16O atom will be exchanged. If we consider the case where the peptide formed is an extremely poor substrate, then the time scale of the reaction can be considered significantly longer than that of the experiment. Therefore, exchange will occur at only one site and the probability that $^{16}O$ is incorporated into the c-terminus will be p and the probability that $^{18}O$ is incorporated into the c-terminus is 1–p. In this case there is a linear relationship between the amount of unlabeled peptides and p (straight line FIG. 3). If we now consider the case where there are two sites at the c-terminus that exchange can occur (i.e. the peptide is a perfect substrate) then the second reaction is independent of the first and a peptide has the probability p of being unlabeled in the second site and the probability 1–p of being labeled there. Using the principle of independent events, the probabilities are multiplicative and therefore the probability that a peptide will be completely unlabeled with $^{18}O$ is $p^2$ and $1-p^2$ of it being fully-labeled.

Hence the labeling follows an $x=y2$ or parabolic relationship. The theoretical curve for this is given as the lower curve in FIG. 3. In comparing the theoretical data with the experimental data from BSA we see close agreement. For simplicity we have only looked at the % $^{16}O$ labeled (inverse labeling), however, a more detailed study of the various labeling states is provided in FIGS. 4a and 4b.

To summarize, it is possible for all peptides to reform the trypsin-peptide complex; it is just the rate at which this complex is formed that is of issue. If the rate is extremely slow, then it appears as though the peptide has only one site on the c-terminus that can be labeled, and thus the labeling is nearly linear with p. If the rate is extremely fast, then we can assume that the reaction reaches equilibrium having two labeling sites, and thus the amount of labeling resembles $p^2$. These two states represent the boundaries over which the extent of labeling can occur during a proteolytic digestion. Both of these functions have been plotted in FIG. 5 and represent theoretical labeling state limits.

From this model a more realistic understanding of the limits of sample encryption can be gained. With reference to FIG. 5a, consider a protein that is digested in ~37% $H_2^{16}O$ and 63% $H_2^{18}O$ (v/v), the corresponding range of relative labeling that peptides would be expected to achieve therefore falls within the two lines and is 15–38%. If we assume an inherent 5% error in the data for confidence then labeling using a 37% $H_2^{16}O$ content will fall within a window between 10% and 43%. Using this 5% confidence, encryptions states based on 5, 37, 68, 88 and 100% $H_2^{16}O$ content (v/v) should be possible and are included in FIG. 5 as gray boxes. There is a 10% (2×5%) vertical gap between these regions. Of course, it is likely that the relative error could be larger. For comparison, a more conservative error estimate of 10% would allow the encryption of only 4 samples based on this model, and an error in the range of 18% would allow for only 3 samples to be encrypted. Rough validation for this model has been obtained from BSA data where the results from five different encryption states are compared with the theoretical curves. The data indicated fairly good agreement with theory confirming the validity of the approach. This was the same data used to generate the experimental curves in FIG. 3. Further confirmation of a simpler system is given in FIG. 5b where 500 fmol digest samples of □-Casein, Phosphorylase B and BSA were digested in 100, 47.5 and 13% $H_2^{16}O$. The examination of the encryption of 4 and 5 states is currently underway in our laboratory.

Although we present a crude hypothesis to explain the nature of the relative labeling efficiency of peptides, it is recognized that more conclusive experiments are needed. Nevertheless, a number of important conclusions from these experiments can be drawn. The first is that the labeling efficiency is dependent on both the relative ratio of $H_2^{16}O/H_2^{18}O$ in a digest buffer mixture and also on the nature of the peptide formed. This is in agreement with other researchers [31-36] but in contrast to some of the earlier work by Shevchenko et al.[18] who suggested that the labeling was independent of the nature of the peptide. More importantly, the data suggests that the broad application of $^{18}O$ labeling as an encryption tool, would be limited to a maximum of five states, but more realistically it is likely that this number is only three or four.

For any advantage gained during the encryption step to be realized a rapid automatable method of decoding the samples must also exist. In this regard, the manual sorting and analysis of data would negate any gains in a true high throughput operation. As such, a computer algorithm must exist that first identifies the peptide with high probability based on mass, then generates a theoretical natural isotope abundance distribution based on this identification, and finally subtracts the relative isotopic contribution by each of the labeled states and compares them in a relative sense to generate the $^{16}O/^{18}O$ ratio of interest. Although the later is fairly straightforward and has already been demonstrated,[39] the former is not as straightforward as it relies both on accurate mass measurements and the ability to identify mass shifted (e.g. +2 and +4 amu) peaks as the parent ion in isotope envelopes that are much more complicated in nature and extend to cover larger mass windows. A further complication is that for protein identification based on MS/MS data using encrypted samples, the sample provenance must be identified in the MS survey-scan prior to MS/MS. Although $^{18}O$ modifications can be included in MSMS database searching programs, for samples with different $^{16}O/^{18}O$ incorporation it would be difficult (useless) to decode samples at this stage unless a wide enough parent ion mass window was selected to pass both labeled and unlabeled isotopic envelopes in their respective ratios.

CONCLUSIONS

The labeling of peptides with $^{18}O$ can be achieved in concert with the tryptic digestion of proteins. It is a very simple and straightforward procedure. The labeling of peptides is dependent on the nature of the peptides formed, digestion conditions and the relative ratio of $^{16}O/^{18}O$ in the digestion buffer mixture. Given the nature of these parameters, the labeling efficiency may vary from digest to digest and from peptide to peptide. The labeled peptides are stable under normal solution conditions described herein and are independent of the relative $^{16}O/^{18}O$ content providing that the tryptic activity is first quenched with the addition of formic acid 1–5% following digestion. As such, labeled samples can be prepared and used in a variety of experimental and analysis dependent solution matrices without significant change to the relative labeling efficiency. This is especially important in considering that MALDI, nanoES or nanoLC each have different solution requirements for efficient operation.

Because of the dependence of labeling efficiency on the nature of the peptide a simple relationship between the relative $^{16}O/^{18}O$ digest buffer mixture content (encryption ratio) and labeling efficiency does not exist. Assuming reasonable error, however, it should be possible to distinguish between peptides batches labeled with 2–5 different encryption states. To properly realize the multi-sample processing capability of encryption, a complementary automated de-encryption program must also exist. The ability to automate the assignment of the relative composition of an isotope envelope in terms of unlabeled, singly labeled and doubly labeled species is possible based on isotope ratios. At present, the computer programs necessary to automatically decode the samples are not commercially available.

Perhaps the most important application of $^{16}O/^{18}O$ labeling is that of a diagnostic for sample processing in proteomics. The Ziptip example cited above shows how one aspect of the sample processing stage can be evaluated. From the above data (Table 5), if we assume that we are able to preconcentrated a sample down to 1 $\mu L$ then our initial 1000, 500, 200, 100 and 50 fmol samples become 700, 350, 100, 15 and ~2 fmol/$\mu L$. This suggests that the benefits of using standard Ziptip protocols for sample cleanup and preconcentration are diminished with samples at the 100-fmol level or below and may not be useful in this range (i.e. an alternative method must be employed). It is interesting to note that similar results were obtained for the regular $C_{18}$Ziptip micropipette tips. Similarly, this approach can be used to evaluate other important sample processing steps, such as gel types, staining protocols, and even recovery vs. the number and dimension of gel lanes on a gel slab. Ultimately the results obtained from these diagnostics will be used to increase detection efficiency, decrease analysis time and reduce costs, which are extremely important considerations in a high throughput environment.

It should be noted that an important consideration in using $^{18}O$ labeling (or any labeling) in a high throughput manner is its associated cost. Sigma-Aldrich currently retails its 95% atom % $^{18}O$ enriched water for ~$1000/gram. From an encryption point of view, this is a costly proposition, from a diagnostic point of view however, it is less so considering that several large batches of standards can be prepared from one sample vial and the savings gained by the development of more efficient processing protocols. A current report on the supply and demand of $^{18}O$ enriched water[41] has indicated that the price is reflected in the increased demand and decreased production of $^{18}O$ water in recent years. It is interesting to note that other commercially available labels such as ICAT (Applied Biosystems, Framingham, CA, USA) cost ~$1000 USD/mg and of which you can get approximately 10 experimental (sample/standard) sets. For 5 protein ID's/day this works out to ~$180 000/year and ~$1.8 million/year for 50 ID's a day. As well, there have been few reports in the literature describing the labeling efficiency, stability and side reactions associated with these labels. Although the numbers listed above are just ballpark figures, they illustrate the important balance between cost effectiveness and efficiency, and as such, further emphasize the need for the careful development of effective sample processing for high throughput proteomics.

These results have demonstrated that sample encryption and sample quantitation can be obtained using the different embodiment of the described methodologies in this application. Furthermore, the power of tandem mass spectrometry can be used to better define the $^{16}O:^{18}O$ ratio for encryption as well as quantitation purposes.

REFERENCES (1) Lopez M. F. *Electrophoresis* 2000, 21, 1082–1093.
(2) Gaevert, K.; Vandekerckhove, J. *Electrophoresis* 2000, 21, 1145–1154.
(3) Corthals, G. L.; Wasinger, V. C.; Hochstrasser, D. F.; Sanchez, J. C. *Electrophoresis* 2000, 21, 1104–1115.
(4) Chalmers, M. J.; Gaskell, S. J. *Curr. Opin. Biotech.* 2000, 11, 384–390.
(5) Pandey, A.; Mann, M. *Nature* 2000, 405, 837–846.
(6) Gygi, S. P.; Corthals, G. L.; Zhang, Y.; Roochon, Y.; Abersold, R. *Proc. Nat. Acad. Sc. USA* 2000, 10, 1073–1078.
(7) Link, A. J.; Eng, J.; Schieltz, D. M.; Carmack, E.; Mize, G. J.; Morris, D. R.; Garvick, B. M.; Yates III, J. R. *Nat. Biotechnol.* 1999, 17, 676–682.
(8) Marie, G.; Serani, L.; Laprevote, O. *Anal. Chem.* 2000, 72, 5423–5430.
(9) Martin, S. E.; Shabanowitz, J.; Hunt, D. F.; Marto, J. A. *Anal. Chem.* 2000, 72, 4266–4274.
(10) Washburn, M. P.; Wolters, D.; Yates III, J. R.; *Nat Biotech.* 2001, 19, 242–247.
(11) Henzel, W. J.; Billeci, T. M.; Stults, J. T.; Wong, S. C.; Grimley, C.; Watanabe, C. *Proc. Natl. Acad. Sci. USA* 1993, 5011–5015.
(12) Wilm, M.; Mann, M. *Anal. Chem.* 1996, 68, 1–8.
(13) Shevchenko, A.; Laboda, A.; Shevchencko, A.; Ens, W.; Standing, K. *Anal. Chem.* 2000, 72, 2132–2141.

(14) Verhaert, P.; Uttenweiler-Joseph, S; de Vries, M.; Laboda, A.; Ens, W.; Standing, K. G. *Proteomics* 2001, 1, 118–131.
(15) Shevchenko, A.; Sunyaev, S.; Laboda, A.; Shevchencko, A.; Bork, P.; Ens, W.; Standing, K. *Anal. Chem.* 2001, 73, ASAP.
(16) Baldwin, M. A.; Medzirhadszky, K. F.; Lock, C. M.; Fisher, B.; Settineri, T. A.; Burlingame, A. L. *Anal. Chem.* 2001, 73, ASAP.
(17) Marina, A.; Garcia, M. A.; Albar, J. P.; Yague, J.; Lopez de Castro, J. A.; Vasquez, J. *J. Mass Spectrom.* 1999, 34, 17–27.
(18) Shevchenko, A.; Chemushvich, I.; Ens, W.; Standing, K.; Thomson, B.; Wilm, M.; Mann, M. *Rapid Commun. Mass Spectrom.* 1997, 11, 1015–1024.
(19) Shevchenko, A.; Wilm, M.; Vorm, O.; Mann, M. *Anal. Chem.* 1996, 68, 850–858.
(20) Sechi, S.; Chait, B. T. *Anal. Chem.* 1998, 70, 5150–5158.
(21) Welinder, K. G. *Anal. Biochem.* 1988, 174, 54–64.
(22) Lundell, N.; Schreitmuller, T. *Anal. Biochem.* 1999, 266, 31–47.
(23) Speicher, K. D.; Kolbas, O.; Harper, S.; Speicher, D. W. *J. Biomol. Tech.* 2000, 11, 74–86.
(24) Erdjument-Bromage, H.; Lui, M.; Lacomis, L.; Grewal, A.; Annan, R. S.; McNulty, D. E.; Carr, S. A.; Tempst, P. *J. Chrom. A* 1998, 826, 167–181.
(25) Gygi, S. P.; Rist, B.; Gerber, S. A.; Turecek, F.; Gelb, M. H.; Abersold, R. *Nat. Biotechnol.* 1999, 17, 994–999.
(26) Gygi, S. P.; Rist, B.; Abersold, R. *Curr. Opin. Biotech.* 2000, 11, 396–401.
(27) Griffin, T. J.; Gygi, S. P.; Rist, B.; Abersold, R.; Laboda, A.; Jilkine, A.; Ens, W.; Standing, K. G. *Anal. Chem.* 2001, 73, 978–986.
(28) Ji, J.; Charkraborty, A.; Geng, M.; Zhang, X.; Amini, A.; Bina, M.; Regnier, F. *J Chrom. B* 2000, 745, 197–210.
(29) Munchbach, M.; Quadroni, M.; Miotto, G.; James, P. *Anal. Chem.* 2000, 72, 4047–4057.
(30) Conrads, T. P.; Alving, K.; Veensta, T. D.; Belov, M. E.; Anderson, G. A.; Anderson, D. J.; Lipton, M. S.; Pasa-Tolic, L.; Udseth, H. R.; Chrisler, W. B.; Thrall, B. D.; Smith, R. D. *Anal. Chem.* 2001, 73, ASAP.
(31) Bender, M. L.; Kemp, K. C. *J. Am. Chem. Soc.* 1957, 79, 116–120.
(32) Sharon, N.; Grisaro, V.; Neuman, H. *Arch. Biochem. Biophys.* 1962, 219–221.
(33) Murphy, R. C.; Clay, K. L. *Biomed. Mass Spectrom.* 1979, 6, 309–314.
(34) Leis, H. J.; Fauler, G.; Windischhofer, W. *Curr. Org. Chem.* 1998, 2, 131–144.
(35) Desiderio, D. M., Kai, M. *Biomed. Mass Spectrom.* 1983, 10, 471–479.
(36) Schnolzer, M.; Jedrzejewski, P.; Lehman, W. D. *Electrophoresis* 1996, 17, 945–953.
(37) Kosaka, T.; Takazawa, T.; Nakamura, T. *Anal. Chem.* 2000, 72, 1179–1185.
(38) Kuster, B.; Mann, M. *Anal. Chem.* 1999, 71, 1431–1440.
(39) Mirgorodskaya, O. A.; Kozmin, Y. P.; Titov, M. I.; Komer, R.; Sonksen C. P.; Roepstorff, P. *Rapid Commun. Mass Spectrom.* 2000, 14, 1226–1232.
(40) Coligan, J. E.; Dunn, B. M.; Ploegh, H. L.; Speicher, D. W.; Wingfield, P. T. *Current Protocols in Protein Science*, Wiley: New York, 1995–2000,
(41) Ad hoc Committee of the North American Society for the Study of Obesity, Report on the supply and demand of $^{18}O$ Enriched water, Jun. 6, 1999.

What is claimed is:

1. A method for encoding a plurality of polypeptide samples for analysis by mass spectrometry, comprising, for each individual sample:
   (i) cleaving the amide backbone of polypeptides in said sample to form sub-populations of fragments having carboxy-terminal residues;
   (ii) mass-modifying the carboxy-terminal residues of said fragments with one of at least two moieties of different molecular weight to produce a plurality of discrete populations of mass-modified fragments which differ in molecular weight by the addition of said moiety, wherein the moieties differ in molecular weight due to inclusion of isotypes of differing molecular weight,
wherein, for each individual sample, the mass-modification produces the plurality of various discrete populations labeled, in a predetermined ratio of said at least two moieties, and which ratio is different from one of said individual samples to the next amongst the plurality of polypeptide samples.

2. A method for encoding a plurality of polypeptide samples for analysis by mass spectrometry, comprising, for each individual sample:
   (i) cleaving the amide backbone of polypeptides in said sample to form sub-populations of fragments having carboxy-terminal lysine or arginine residues;
   (ii) mass-modifying the carboxy-terminal residues of a first portion of said fragments with a first moiety, and mass-modifying the carboxy-terminal residues of a second portion of said fragments with a second moiety, wherein the two moieties have different molecular weights, and the ratio between the first and second portions of said fragments are predetermined;
   (iii) combining the two portions produced in (ii) and producing a plurality of discrete populations of mass-modified fragments which differ in molecular weight by the difference in molecular weight between the first and second moieties,
wherein, for each individual sample, the mass-modification produces the various discrete populations reflecting said predetermined ratio, and which ratio is different from one of said individual samples to the next amongst the plurality of polypeptide samples.

3. The method of claim 1, wherein the moieties are selected from halide, phosphate, amine, alkyl, thiol, or hydroxyl moieties.

4. The method of claim 1 or 3, wherein the moieties are added by modification of a carboxyl group of said carboxy terminal residue.

5. The method of claim 1, wherein the moieties are added by modification of an amine group of said lysine or arginine residue.

6. The method of claim 1, wherein enzymatic digestion is used to cleave the amide backbone of the polypeptides.

7. The method of claim 6, wherein the enzymatic digestion includes treatment of the polypeptides with an enzyme which produces a carboxy terminal lysine and/or arginine residue, such as selected from the group of trypsin, Arg-C and Lys-C, or a combination thereof.

8. The method of claim 1 or 6, wherein cleavage of the amide backbone of the polypeptides and the mass modification are carried out in the same reaction mixture.

9. The method of claim 1 or 6, wherein cleavage of the amide backbone of the polypeptides and the mass modification are carried out in separate reaction mixture.

10. The method of claim 1, wherein said fragments are separated based on size, solubility, electric charge and/or ligand specificity prior to ionization.

11. The method of claim 10, wherein said fragments are separated using one or more procedures selected from the group of gel-filtration, isoelectric precipitation, electrophoresis, isoelectric focusing, ion exchange chromatography, and affinity chromatography.

12. The method of claim 10, wherein said fragments are separated using high performance liquid chromatography.

13. The method of claim 1, further comprising:
    (iii) analyzing the molecular weights of said fragments by mass spectrometry.

14. The method of claim 1, further comprising:
    (iii) ionizing said fragments to produce gas phase ions;
    (iv) further fragmenting the gas phase ions under conditions which produce a population of daughter ions of incremental molecular weight, which population of daughter ions results substantially from fragmentation of the amide backbone of said fragments;
    (v) determining the molecular weight of said gas phase ions and daughter ions by mass spectrometry; and
    (vi) determining the sequence of at least a portion of the test peptide or test peptide or test polypeptide from the determined molecular weights.

15. The method of claim 13 or 14, wherein the mass spectrometry method used is selected from fast atomic bombardment (FAB), plasma desorption (PD), thermospray (TS), electrospray (ES) and matrix assisted laser desorption (MALDI).

16. The method of claim 2, wherein the moieties are selected from halide, phosphate, amine, alkyl, thiol, or hydroxyl moieties.

17. The method of claim 2 or 16, wherein the moieties are added by modification of a carboxyl group of said lysine or arginine residue.

18. The method of claim 2 or 16, wherein the moieties are added by modification of an amine group of said lysine or arginine residue.

19. The method of claim 2, wherein enzymatic digestion is used to cleave the amide backbone of the polypeptides.

20. The method of claim 19, wherein the enzymatic digestion includes treatment of the polypeptides with an enzyme selected from the group of trypsin, Arg-C and Lys-C, or a combination thereof.

21. The method of claim 2 or 19, wherein cleavage of the amide backbone of the polypeptides and the mass modification are carried out in the same reaction mixture.

22. The method of claim 2 or 19, wherein cleavage of the amide backbone of the polypeptides and the mass modification are carried out in separate reaction mixture.

23. The method of claim 2, wherein said fragments are separated based on size, solubility, electric charge and/or ligand specificity prior to ionization.

24. The method of claim 23, wherein said fragments are separated using one or more procedures selected from the group of gel-filtration, isoelectric precipitation, electrophoresis, isoelectric focusing, ion exchange chromatography, and affinity chromatography.

25. The method of claim 23, wherein said fragments are separated using high performance liquid chromatography.

26. The method of claim 2, further comprising:
    (iv) analyzing the molecular weights of said fragments by mass spectrometry.

27. The method of claim 2, further comprising:
    (iv) ionizing said fragments to produce gas phase ions;
    (v) further fragmenting the gas phase ions under conditions which produce a population of daughter ions of incremental molecular weight, which population of daughter ions results substantially from fragmentation of the amide backbone of said fragments;
    (vi) determining the molecular weight of said gas phase ions and daughter ions by mass spectrometry; and
    (vii) determining the sequence of at least a portion of the test peptide or test peptide or test polypeptide from the determined molecular weights.

28. The method of claim 26 or 27, wherein the mass spectrometry method used is selected from fast atomic bombardment (FAB), plasma desorption (PD), thermospray (TS), electrospray (ES) and matrix assisted laser desorption (MALDI).

29. A method for quantitating the abundance of a given polypeptide present in a sample using mass spectrometry, comprising of:
    (i) cleaving the amide backbone of polypeptides in said sample to form sub-populations of fragments having carboxy-terminal lysine or arginine residues;
    (ii) cleaving the amide backbone of a standard sample of said given polypeptide to form sub-populations of fragments having carboxy-terminal lysine or arginine residues;
    (iii) mass-modifying the carboxy-terminal residues of fragments generated in step (i) with a first moiety, and mass-modifying the carboxy-terminal residues of fragments generated in step (ii) with a second moiety, wherein the two moieties have different molecular weights;
    (iv) combining the two portions produced in (iii), and subjecting the peptide sample to analysis by mass spectrometry to generate mass spectra comprising at least one signal doublet for each fragment, the signal doublet comprising a first signal and a second signal shifted a known units from the first signal, wherein said known units is the difference in molecular weight between the two said moieties;
    (iii) determining a signal ratio for at least one fragment pair by relating the difference in signal intensity or area between the first signal and the second signal;
    whereby the abundance of the given polypeptide is determined from the said signal ratio and the known amount of said standard sample of the given polypeptide, based on the principle that signal intensity is proportional to peptide abundance.

30. The method of claim 29, wherein the first and second moieties used are different isotopes of the same atom.

31. The method of claim 30, wherein the isotopes used are $^{16}O$ and $^{18}O$ in $H_2O$.

32. The method of claim 29, wherein enzymatic digestion is used to cleave the amide backbone of the polypeptides.

33. The method of claim 32, wherein the enzymatic digestion includes treatment of the polypeptides with an enzyme selected from the group of trypsin, Arg-C and Lys-C, or a combination thereof.

34. The method of claim 29, wherein cleavage of the amide backbone of the polypeptides and the mass modification are carried out in the same reaction mixture.

35. The method of claim 29, wherein cleavage of the amide backbone of the polypeptides and the mass modification are carried out in separate reaction mixture.

36. The method of claim 29, wherein the mass spectrometry method used is selected from fast atomic bombardment (FAB), plasma desorption (PD), thermospray (TS), electrospray (ES) and matrix assisted laser desorption (MALDI).

37. The method of claim 1, 2, or 29, wherein for each individual sample, a first protease is used to digest all polypeptides within said each individual sample before step (i).

38. The method of claim 37, wherein about 100 nL or less of all digested polypeptides from said each individual sample is adsorbed in a capillary and/or chromatographic materials therein, and a second protease is used to further cleave the amide backbone of the adsorbed polypeptides in step (i) at the presence of said first and/or said second moiety.

39. The method of claim 38, wherein the first protease is Lys-C, the second protease is trypsin.

40. The method of claim 38, wherein before adding the second protease, the adsorbed polypeptides are washed one or more times with a buffer.

41. The method of claim 13, 14, 26, or 27, wherein pulsing is used to boost the signal of one or more of said fragments, or one or more of said gas phase ions and daughter ions.

* * * * *